US008246677B2

(12) United States Patent  
Ryan

(10) Patent No.: US 8,246,677 B2  
(45) Date of Patent: Aug. 21, 2012

(54) DELIVERY SYSTEMS AND METHODS OF IMPLANTATION FOR REPLACEMENT PROSTHETIC HEART VALVES

(75) Inventor: Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1163 days.

(21) Appl. No.: 12/070,382

(22) Filed: Feb. 15, 2008

(65) Prior Publication Data

US 2008/0228254 A1 Sep. 18, 2008

Related U.S. Application Data

(60) Provisional application No. 60/901,787, filed on Feb. 16, 2007.

(51) Int. Cl.
*A61F 2/06* (2006.01)
*A61F 2/24* (2006.01)

(52) U.S. Cl. ............... 623/1.26; 623/1.24; 623/2.11; 623/2.17

(58) Field of Classification Search ............ 623/2.11, 623/2.13, 2.17, 1.11, 1.24, 1.26, 2.12–2.19
See application file for complete search history.

(56) References Cited

U.S. PATENT DOCUMENTS

| | | | |
|---|---|---|---|
| 4,106,129 A | 8/1978 | Carpentier et al. | |
| 4,921,484 A * | 5/1990 | Hillstead | 604/104 |
| 5,037,434 A | 8/1991 | Lane | |
| 6,168,614 B1 | 1/2001 | Andersen et al. | |
| 7,195,641 B2 | 3/2007 | Palmaz et al. | |
| 2005/0137682 A1* | 6/2005 | Justino | 623/1.24 |
| 2005/0251251 A1 | 11/2005 | Cribier | |
| 2006/0052867 A1 | 3/2006 | Revuelta et al. | |
| 2006/0074484 A1 | 4/2006 | Huber | |
| 2006/0149360 A1 | 7/2006 | Schwammenthal et al. | |
| 2007/0043435 A1 | 2/2007 | Seguin et al. | |
| 2008/0004696 A1 | 1/2008 | Vesely | |

FOREIGN PATENT DOCUMENTS

| | | |
|---|---|---|
| EP | 1 671 608 | 6/2006 |
| WO | 2007/013999 | 2/2007 |
| WO | 2007/053243 | 5/2007 |
| WO | 2007/071436 | 6/2007 |
| WO | 2007/081820 | 7/2007 |
| WO | 2007/130537 | 11/2007 |

OTHER PUBLICATIONS

Bonhoeffer, et al, "Transcatheter Implantation of a Bovine Valve in Pulmonary Position," Circulation, 2002; 102:813-816.
Bonhoeffer, et al., "Percutaneous Insertion of the Pulmonary Valve," J. Am. Coll. Cardiol., 2002; 39:1664-1669.

(Continued)

*Primary Examiner* — Corrine M McDermott
*Assistant Examiner* — Melissa Ryckman

(57) ABSTRACT

A method of delivering a replacement prosthetic valve to a previously implanted prosthetic valve including the steps of compressing a replacement prosthetic valve having an expandable stent within a sheath of a delivery system, wherein the delivery system comprises a proximal end, a distal end, and a centering structure positioned between the proximal and distal ends, advancing the delivery system and compressed replacement prosthetic valve into a vessel of a patient until the distal end of the delivery system is positioned adjacent to a second side of a previously implanted prosthetic valve, deploying the centering structure to radially reposition the distal end of the delivery system, further advancing the delivery system toward the previously implanted prosthetic valve, and deploying the replacement prosthetic valve.

7 Claims, 10 Drawing Sheets

OTHER PUBLICATIONS

Cribier, et al., "Percutaneous Transcatheter Implantation of an Aortic Valve Prosthesis for Calcific Aortic Stenosis," Circulation, 202; 106:3006-3008.

Boudjemline, et al., "New insights in minimally invasive valve replacement: description of a cooperative approach for the off-pump replacement of mitral valves," European Heart Journal (2005) 26, 2013-2017.

Walther, et al., "Valve-in-a-Valve Concept for Transcatheter Minimally Invasive Repeat Xenograft Implantation," JACC, vol. 50, No. 1, 2007, Jul. 3, 2007:56-60.

* cited by examiner

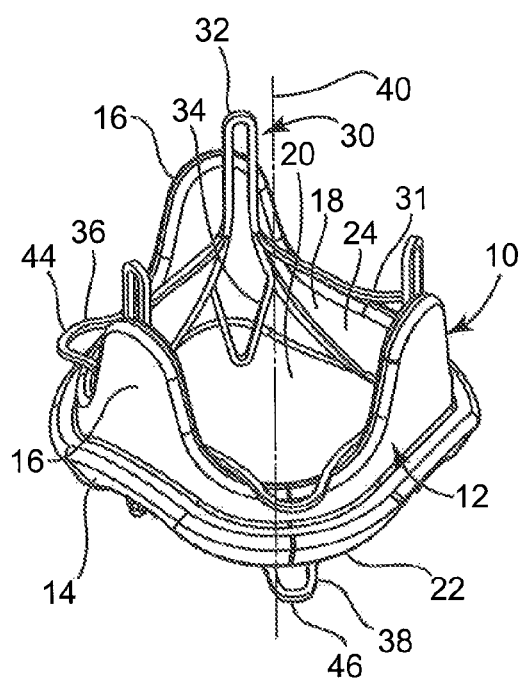
Fig. 1
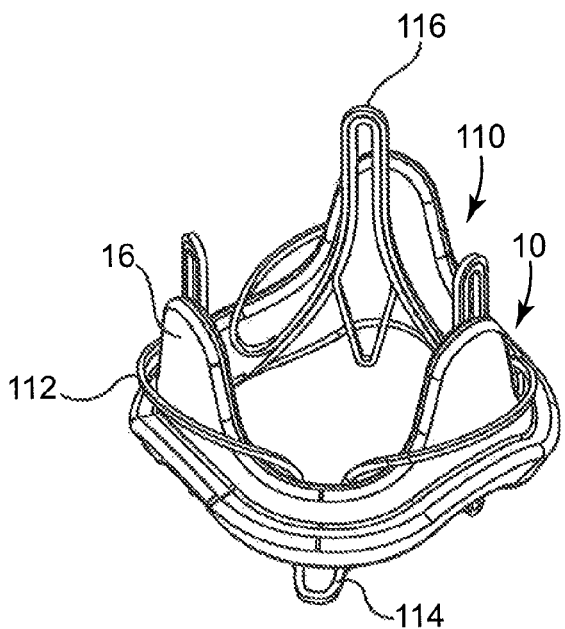
Fig. 2
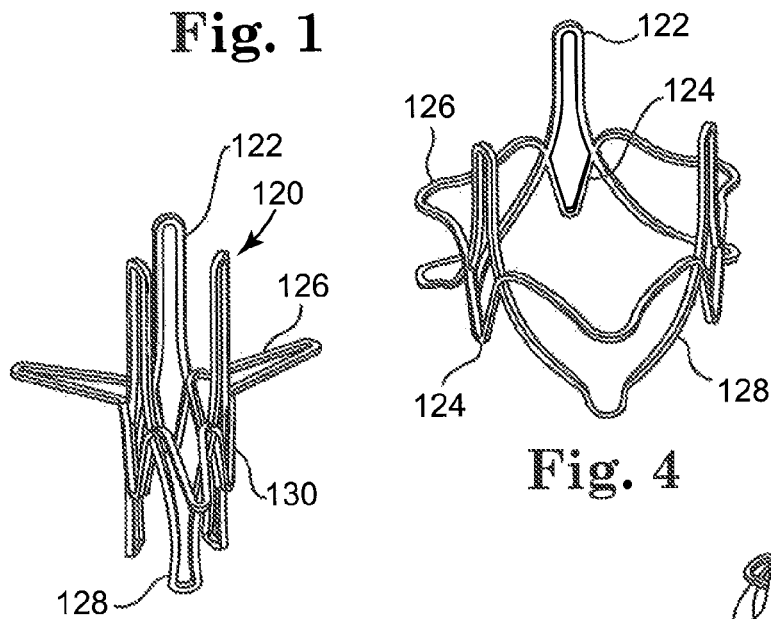
Fig. 3
Fig. 4
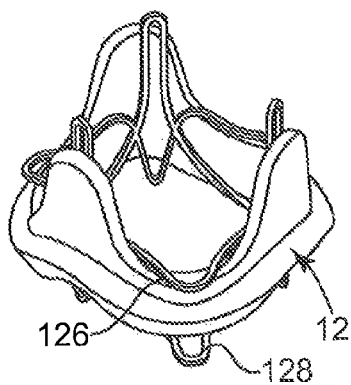
Fig. 5

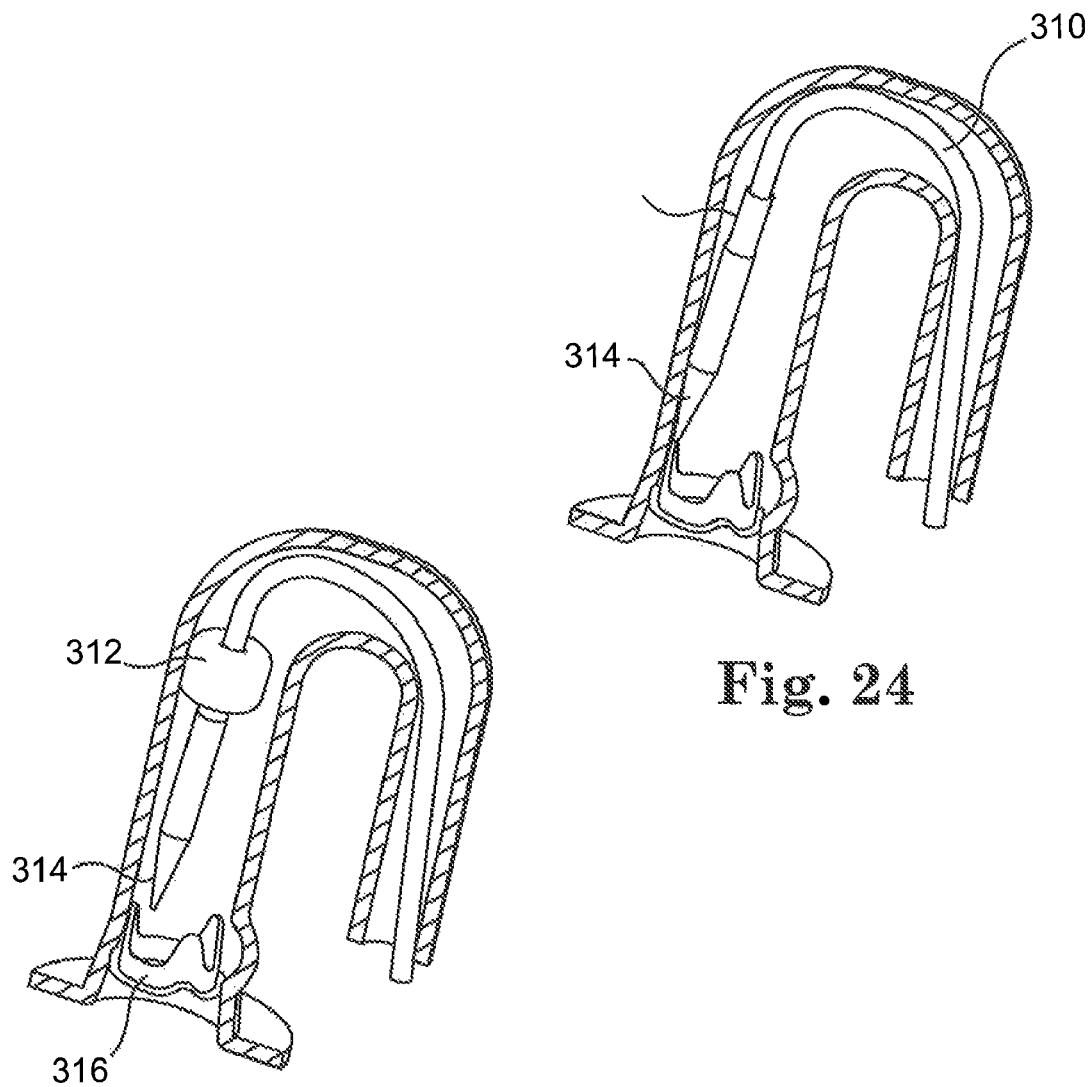
Fig. 24
Fig. 25
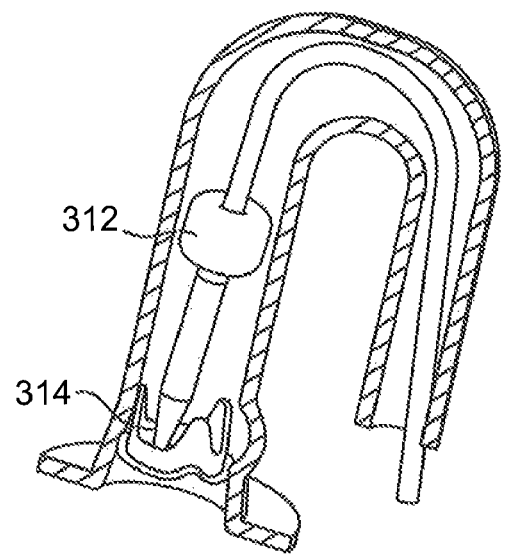
Fig. 26

DELIVERY SYSTEMS AND METHODS OF IMPLANTATION FOR REPLACEMENT PROSTHETIC HEART VALVES

CROSS-REFERENCE TO RELATED APPLICATION

The present application claims priority to U.S. Provisional Application No. 60/901,787, filed Feb. 16, 2007, and titled "Replacement Prosthetic Heart Valve Including Delivery System and Method of Implantation", the entire contents of which is incorporated herein by reference in its entirety.

TECHNICAL FIELD

The present invention relates to prosthetic heart valves. More particularly, it relates to devices, methods, and delivery systems for percutaneously implanting prosthetic heart valves.

BACKGROUND

Various types and configurations of prosthetic heart valves are used to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses.

As used throughout this specification a "prosthetic heart valve" is intended to encompass bioprosthetic heart valves having leaflets made of a biological material (e.g., harvested porcine valve leaflets, or bovine or equine pericardial leaflets), along with synthetic leaflet materials or other materials. These bioprosthetic heart valves typically include a stent having a substantially circular base (or stent ring), around which an annular suture material is disposed for suturing the prosthesis to heart tissue. The stent further typically includes at least two, but typically three, support structures extending from the stent ring. These support structures are commonly referred to as stent posts or commissure posts. These posts typically are rigid yet somewhat flexible structures extending from the stent ring, which are covered by a cloth-like material similar to that of the annular suture material. The stent or commissure posts define the juncture between adjacent tissue or synthetic leaflets otherwise secured thereto. Examples of bioprosthetic heart valves are described in U.S. Pat. Nos. 4,106,129 (Carpentier et al.), and 5,037,434 (Lane), the entire disclosures of which are incorporated herein by reference. These disclosures describe a conventional configuration of three leaflets, with one leaflet disposed between each pair of stent or commissure posts. Regardless of whether a stent is provided, however, bioprosthetic heart valves are generally tubular so that when the leaflets are in an open position, an internal passage is defined through which blood can flow.

The bioprosthetic heart valves further typically include a sewing ring or suture ring that provides a means for fixing the prosthetic heart valve to the patient's native heart valve orifice tissue (e.g., native annulus or valvular rim) that is associated with the native heart valve being repaired or replaced. In particular, an exacting surgical implantation technique is traditionally employed whereby the heart is stopped (i.e., cardiopulmonary bypass) and opened, which is followed by surgical removal of damaged or diseased natural valve structure. A prosthetic heart valve can then be oriented within the native valvular area, with the sewing ring being seated against or at the native annulus or valvular rim. Sutures are then used to affix the sewing ring to the natural tissue. Obviously, the risks associated with this invasive type of surgery are numerous, particularly when cardiopulmonary bypass procedures are used.

A successfully implanted prosthetic heart valve will normally function without problems for many years. In certain instances, however, deficiencies may become evident shortly after implant or within a few years, particularly in younger patients. Common functional deficiencies include the calcification of the prosthetic heart valve leaflets, stenosis, and prosthetic heart valve insufficiency. Under these and other circumstances, the prosthetic heart valve does not function properly and conventionally requires surgical removal and replacement. Surgical removal of such a previously implanted prosthetic heart valve entails the same invasive surgical intervention described above, coupled with the need to remove the old prosthetic valve and implant a new prosthetic heart valve. In addition, the risk of mortality is often higher when performing a second surgery in the same area of the body, particularly when performing heart-related surgeries. Another disadvantage to this additional surgery is that the reopening of a sternotomy has been known to have a relatively high risk of causing an infection.

Thus, while these types of surgeries are well-accepted, the conventional surgical intervention described above is difficult to perform and can result in patient injury or more severe complications. In fact, due to physical weakness of a patient, implantation of a prosthetic heart valve via the conventional surgical technique may be considered too high-risk or contraindicated for certain patients. Further, removal of a previously implanted prosthetic heart valve requires cutting of the sutures that secure the prosthesis to the native annulus/valvular rim, and attachment of a new sewing ring via stitching, which can further compromise the integrity of the valvular rim and lead to recovery complications, morbidity, and mortality.

Although not necessarily related to the specific prosthetic heart valve replacement concerns described above, efforts have also been made to devise a prosthetic heart valve capable of being delivered percutaneously via transcatheter implantation, thereby avoiding the complications and risks associated with conventional surgical intervention. For example, in U.S. Pat. No. 6,168,614 (Andersen et al.), a heart valve prosthesis is described for implantation in the body by use of a catheter. The valve prosthesis consists of a support structure with a tissue valve connected to it, whereby the support structure is delivered in a collapsed state through a blood vessel and secured to a desired valve location with the support structure in an expanded state.

Other percutaneously-delivered prosthetic heart valves have been suggested having a generally similar configuration, such as by Bonhoeffer, P. et al., "*Transcatheter Implantation of a Bovine Valve in Pulmonary Position.*" Circulation, 2002; 102:813-816, and by Cribier, A. et al. "*Percutaneous Transcatheter Implantation of an Aortic Valve Prosthesis for Calcific Aortic Stenosis.*" Circulation, 2002; 106:3006-3008, the disclosures of which are incorporated herein by reference. These techniques rely at least partially upon a frictional type of engagement between the expanded support structure and the native tissue to maintain a position of the delivered prosthesis, although the stents can also become at least partially embedded in the surrounding tissue in response to the radial force provided by the stent and any balloons used to expand the stent. Thus, with these transcatheter techniques, conventional sewing of the prosthetic heart valve to the patient's native tissue is not necessary. Similarly, in an article by Bonhoeffer, P. et al. titled "*Percutaneous Insertion of the Pulmonary Valve*." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Devices and methods have more recently been developed for percutaneously replacing deficient, previously implanted prosthetic heart valves, which are described, for example, in U.S. Patent Publication No. 2006/0052867 (Revuelta et al.), the entire disclosure of which is incorporated herein by reference. Other transcatheter technologies for delivering replacement valves are described in PCT Application Nos. WO 2007/053243-A2, WO 2007/130537-A1, and WO 2007/081820-A1; United States Patent Application Publication Nos. 2005/0251251-A1, 2007/0043435-A1, and 2008/0004696-A1; and U.S. Pat. No. 7,195,641. However, a need exists for additional delivery systems, and related methods of implanting replacement heart valves, that are conducive to percutaneous delivery for replacing a deficient, previously implanted bioprosthetic heart valve.

SUMMARY

The delivery systems of the invention can be used with a number of different configurations of replacement valves that provide complimentary features to promote physical docking or connection of the replacement heart valve to a previously implanted prosthetic heart valve, such as the aortic valve, mitral valve, pulmonic valve, and/or tricuspid valve. In some embodiments, the delivery systems and related methods of implantation of the invention utilize a previously implanted prosthetic heart valve as a platform to facilitate mounting relative to a native heart valve. Thus, the delivery systems of the invention are amenable to percutaneous delivery via either a transarterial or apical approach (either with or without cardiopulmonary bypass). Further, in cases where a previously implanted prosthetic heart valve is being functionally replaced, the deficient prosthetic heart valve need not be physically removed from the patient. Thus, the systems for delivering replacement heart valves of the present invention can be used at any point during the "useful life" of a conventional prosthetic heart valve. Further, the methodology associated with the present invention can be repeated multiple times, such that the delivery systems of the invention can be used to deliver multiple prosthetic heart valves on top of or within one another, if necessary or desired.

The delivery systems of the invention include features for engagement with a stent to which a valve structure is attached. These stents can include a wide variety of structures and features that can be used alone or in combination with features of other stents and/or heart valves. In particular, these stents provide a number of different docking and/or anchoring structures that cooperate with the structure of a previously implanted prosthetic heart valve, and are conducive to percutaneous delivery thereof. Many of the structures are thus compressible to a relatively small diameter for percutaneous delivery to the heart of the patient using the delivery systems and implantation methods of the invention, and then are expandable through another movement or action of the delivery system.

Methods for insertion of the replacement heart valves of the invention include delivery systems that can maintain the stent structures in their compressed state during their insertion and allow or cause all or specific features of the stent structures to expand once they are in their desired location. The methods may include implantation of the stent structures using either an antegrade or retrograde approach. Further, in many of the delivery approaches of the invention, the stent structure is rotatable in vivo to allow the stent structure to be positioned in a desired orientation.

BRIEF DESCRIPTION OF THE DRAWINGS

The present invention will be further explained with reference to the appended Figures, wherein like structure is referred to by like numerals throughout the several views, and wherein:

FIG. 1 is a perspective view of a prosthetic heart valve with a stent of a replacement prosthetic heart valve positioned therein;

FIG. 2 is a perspective view of a prosthetic heart valve with another exemplary embodiment of a stent of a replacement prosthetic heart valve positioned therein;

FIG. 3 is a perspective view of another exemplary embodiment of a stent of a replacement heart valve, with the stent in a partially compressed state;

FIG. 4 is a perspective view of the stent of FIG. 3 in its expanded state;

FIG. 5 is a perspective view of the stent of FIGS. 3 and 4 as positioned relative to a prosthetic heart valve;

FIGS. 24-26 are partial cross-sectional side views of three sequential steps for delivering a stent to a prosthetic heart valve, including a balloon for centering the delivery system within the heart vessel;

DETAILED DESCRIPTION

Figure 6:
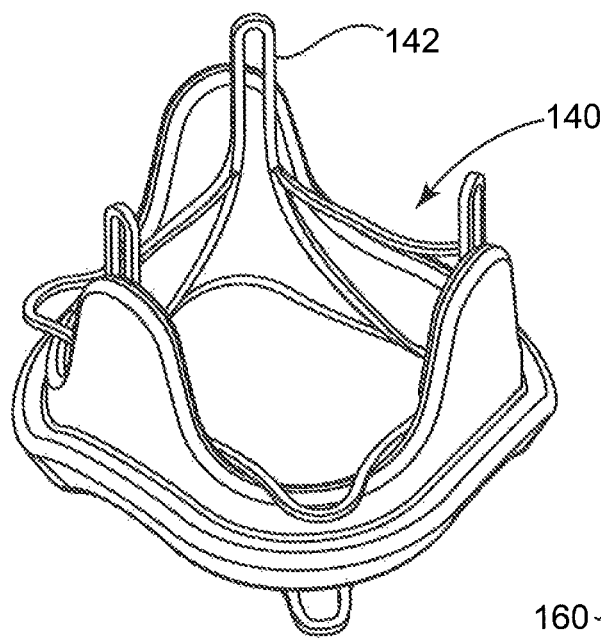
FIG. 6 is a perspective view of another exemplary embodiment of a stent of a replacement valve positioned within a prosthetic heart valve.

The delivery systems and methods of the invention can be used with heart valves having a wide variety of configurations, a number of which are described below. In many cases, only the stent portion of a heart valve is illustrated, although it is understood that multiple leaflets will typically be attached within the interior portion of each stent so that it can perform as a valve. In some cases, these stents are described and illustrated as being positioned relative to a previously implanted prosthetic heart valve, where the stents can be delivered using one or more of the delivery systems and methods described herein.

Referring now to the Figures, wherein the components are labeled with like numerals throughout the several Figures, and initially to FIG. 1, a prosthetic heart valve 10 is illustrated with a stent 30 of the invention positioned therein, which will be described in further detail below. However, referring specifically to the prosthetic heart valve 10, this valve 10 is a typical configuration of a valve that can be implanted within the heart of a patient, such as by suturing or otherwise securing the valve 10 into the area of a native heart valve of a patient. The native heart valves referred to herein can be any of the human heart valves (i.e., mitral valve, tricuspid valve, aortic valve, or pulmonary valve), wherein the type and orientation of an implanted (e.g., surgically implanted) prosthetic heart valve 10 will correspond with the particular form, shape, and function of the native heart valve in which it is implanted.

Valve 10 generally includes a valve structure 12 including a stent ring 14 from which three stent posts or commissure posts 16 extend. All or a portion of the valve structure 12, including the stent ring 14 and stent posts 16, can be covered by a flexible covering 18, which may be a tissue, polymer, fabric, cloth material, or the like to which leaflets (not shown) of the heart valve 10 are attached, such as by sewing. Further, as is known in the art, the internal structure of each of the stent posts 16 can be formed of a stiff but somewhat resiliently bendable material. This construction allows the stent posts 16 to be moved from the orientation shown in FIG. 1 to a deflected orientation by the application of an external force. Once this external force is removed or reduced, the stent posts 16 can then move back toward the orientation shown in FIG. 1.

The valve structure 12 is generally tubular in shape, defining an internal area 20 (referenced generally) that extends from an inflow end 22 to an outflow end 24. The internal area 20 is essentially surrounded by the valve structure 12, and the leaflets attached within the valve structure 12 selectively allow for fluid flow into or out of the lumen of the natural heart valve in which it is implanted. That is, the internal area 20 is alternatively open and closed to the lumen of the natural heart valve in which it is inserted via movement of leaflets. In some patients, the prosthetic heart valve 10 will have previously been implanted in a patient using typical surgical techniques, whereby the stent ring 14 is sewn or attached to the annulus or valvular rim of the native heart valve. Alternatively, the prosthetic valve could have been previously placed in the patient using minimally invasive techniques for holding the valve in place, such as U-clips, for example, or a wide variety of other techniques and features used for minimally invasive and/or percutaneous implantation of the initial prosthetic heart valve.

The prosthetic heart valves (e.g., heart valve 10) used in accordance with the delivery systems and methods of the invention may include a wide variety of different configurations, such as a prosthetic heart valve that has tissue leaflets, or a synthetic heart valve that has polymeric leaflets. In this way, the delivery systems can be used with prosthetic heart valves that are specifically configured for replacing any heart valve. That is, while much of the description herein refers to replacement of aortic valves, the delivery systems of the invention can also generally be used for replacement of tricuspid valves, delivery of venous valves, or for replacing a failed bioprosthesis, such as in the area of an aortic valve or mitral valve, for example. The delivery systems of the invention can also be used for functionally replacing stentless prosthetic heart valves.

The delivery systems of the invention are used for delivering a replacement prosthetic heart valve relative to a previously implanted prosthetic heart valve, which may be configured as the heart valve 10 shown and described herein. This would become a desirable procedure in cases where it is determined that a previously implanted prosthetic heart valve is functionally deficient due to one or more of a variety of factors, such as stenosis, valve failure, inflammation, native valve insufficiency, etc. Regardless of the cause of the deficiency, rather than removing the previously implanted prosthetic heart valve and implanting a second, similarly formed prosthetic heart valve via relatively complicated and invasive open heart surgical techniques, the delivery systems and methods of the present invention leave the deficient previously implanted prosthetic heart valve in place, and the new prosthetic heart valve is deployed so that it functionally replaces the previously implanted prosthetic heart valve. Prior to implanting the new prosthetic valve, the leaflets of the previously implanted and deficient prosthetic heart valve can either be removed using a variety of techniques such as cutters, lasers, and the like, or the leaflets may instead be left in place within the deficient valve, where they will likely be pushed toward the walls of the vessel upon implantation of the new valve.

One embodiment of a stent 30, which can be used as a component of a prosthetic heart valve in accordance with the present invention, is shown in FIG. 1. Stent 30 includes a support structure 31 comprising a number of strut or wire portions arranged relative to each other to provide secure coupling between the stent 30 and a prosthetic heart valve 10 in which it is located. In addition; stent 30 provides a semi-rigid frame for the leaflets of the replacement heart valve, which will be attached in some way within the interior portion of stent 30. Details of several configurations of the stents of the invention are described below; however, in general terms, the stents described herein are generally a series of wires arranged into a tubular support structure, and leaflets can be secured to the interior of the support structure. The leaflets can be formed from a variety of materials, such as autologous tissue, xenograph material, synthetics, or the like, as known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled and attached to a stent support structure. The support structures shown and described relative to the Figures are generally configured to accommodate three leaflets and replace a heart valve (e.g., heart valve 10) that has three commissure posts that accommodate a three-leaflet structure. However, the replacement prosthetic heart valves can incorporate more or less than three leaflets.

In more general terms, the delivery systems and methods of the invention can be used for many different devices that combine a support structure with one or more leaflets to assume configurations that differ from those shown and described, including any known prosthetic heart valve design. In one embodiment, a stent support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "*Percutaneous Insertion of the Pulmonary Valve*", Pediatric Cardiology, 2002; 39:1664-1669; Andersen H R, et al., "*Transluminal Implantation of Artificial Heart Valves*", EUR Heart J., 1992; 13:704-708; Andersen, H. R., et al., "*Transluminal Catheter Implantation of New Expandable Artificial Cardiac Valve*", EUR Heart J., 1990, 11: (Suppl) 224a; Hilbert S. L., "*Evaluation of Explanted Polyurethane Trileaflet Cardiac Valve Prosthesis*", J Thorac Cardiovascular Surgery, 1989; 94:419-29; Block P C, "*Clinical and Hemodyamic Follow-Up After Percutaneous Aortic Valvuloplasty in the Elderly*", The American Journal of Cardiology, Vol. 62, Oct. 1, 1998; Boudjemline, Y., "*Steps Toward Percutaneous Aortic Valve Replacement*", Circulation, 2002; 105:775-558; Bonhoeffer, P., "*Transcatheter Implantation of a Bovine Valve in Pulmonary Position, a Lamb Study*", Circulation, 2000:102: 813-816; Boudjemline, Y., "*Percutaneous Implantation of a Valve in the Descending Aorta In Lambs*", EUR Heart J, 2002; 23:1045-1049; and Kulkinski, D., "*Future Horizons in Surgical Aortic Valve Replacement: Lessons Learned During the Early Stages of Developing a Transluminal Implantation Technique*", ASAIO J, 2004; 50:364-68).

The stent 30 comprises a support structure 31 that is made up of a number of struts or wire segments arranged to provide desired docking or engagement features, which may include individual struts or wire segments arranged and secured to each other, or the support structure 31 may instead be formed from a single piece of material (e.g., a tube of material that is machined to provide the structure shown). In FIG. 1, stent 30 is shown as being positioned within a heart valve 10, which typically would have been previously implanted in a patient. Stent 30 comprises a support structure 31 having multiple upper vertical members 32 spaced apart from each other around the perimeter of the support structure 31, and a corresponding number of lower vertical members 34. Both the upper and lower vertical members 32, 34 extend in a direction that is generally parallel to a longitudinal axis 40 of the support structure 31, and help to define the generally cylindrical shape of the support structure 31. Upper vertical members 32 extend generally toward the outflow end 24 of the valve structure 12, and the lower vertical members 34 extend in a direction that is generally opposite to the direction of the upper vertical members 32, which is toward the inflow end 22 of the valve structure 12.

Each of these upper and lower vertical members 32, 34 are preferably spaced from adjacent upper and lower vertical members 32, 34, respectively, by a distance that is similar or identical to the distance that the stent posts (e.g., stent posts 16) are spaced from each other in a corresponding implanted heart valve (e.g., heart valve 10). Thus, both the number of upper vertical members 32 and the number of lower vertical members 34 are typically the same as the number of stent posts. However, it is possible that the number of upper and lower vertical members 32, 34 are not the same as each other and/or not the same as the number of stent posts.

The upper vertical members 32 are designed to have a height that allows them to have a desired amount of contact with a corresponding stent post. The upper vertical members 32 may extend at least slightly beyond the tops of the stent posts, or may be at least slightly shorter than the stent posts. The lower vertical members 34 may also have any length that allows them to have a desired amount of contact with their corresponding stent posts 16 and other portions of the stent structure 12 with which they come into contact. Again, the lower vertical members 34 may extend at least slightly below the bottom of the stent structure (i.e., stent ring 14 of FIG. 1), or may be at least slightly shorter so that they do not extend below any portion of the stent structure. The selection of the length of these upper and lower vertical members 32, 34 can vary widely, depending on the configuration of the valve structure and the amount of contact desired between the support structure 31 and the interior portion of the stent or valve structure. In any case, the height of upper and lower vertical members 32, 34 should be adequate to provide sufficient contact between the support structure 31 and the corresponding heart valve in which it is positioned to keep the stent 30 in place relative to the heart valve. In addition, the arrangement of upper and lower vertical members 32, 34 should provide sufficient structural integrity to the support structure 31 so that it is resistant to deformation or other changes that impact its effectiveness as a stent structure.

The upper and lower vertical members 32, 34 may be generally "U" or "V" shaped, as illustrated, with the distance between opposite "legs" or extending portions of the members being chosen to provide desired characteristics to the support structure 31. For example, in FIG. 1, the upper vertical members 32 are preferably narrow enough that they will not unintentionally engage with the top edge of corresponding stent posts 16, but are preferably wide enough that they provide adequate contact with the interior portion of the stent posts 16 to help keep the stent 30 in place. In other words, the distance between opposite legs of the "U" or "V" shaped structure is preferably not so large that the members 32 can latch onto the stent posts 16, but is preferably large enough to provide contact between the members 32 and some portion of the interior surface of the stent posts 16. This "U" or "V" shaped structure of these members 32, 34 is particularly adaptable to the configuration where the support structure 31 is essentially a continuous wire structure; however, if the support structure is configured in another manner (e.g., with separate components that are not wire-like), each of the members 32, 34 may essentially consist of a single, relatively solid extending structure, for example. These structures may be arranged and connected relative to each other in a similar configuration to that described relative to a wire structure.

As shown in FIG. 1, heart valve 10 includes three stent posts 16 that are spaced generally at an equal distance from each other around the perimeter of the valve 10 (i.e., approximately 120 degrees apart). These stent posts 16 will generally correspond with the commissures of leaflets of the valve (not shown). It is understood, however, that the stent posts 16 may instead be unevenly spaced from each other. In one example of such an embodiment, first and second stent posts 16 may be spaced from each other by approximately 120 degrees, second and third stent posts 16 may be spaced from each other by approximately 115 degrees, so that first and third stent posts 16 would be spaced from each other by approximately 125 degrees. Other arrangements that vary slightly or substantially from this arrangement may alternatively be used; particularly in cases where more or less than two stent posts 16 are used. One example of such an arrangement would be in the case of a two-leaflet valve (e.g., the mitral valve), which would only include two stent posts arranged at approximately 180 degrees from each other and a corresponding arrangement for its support structure 31.

Support structure 31 further includes multiple upper flange or petal portions 36, each of which is located generally between two adjacent upper vertical members 32, and multiple lower flange or petal portions 38, each of which is located generally between two adjacent lower vertical members 34. The upper and lower flange portions 36, 38 are provided for engagement with the stent or valve structure 12 on generally opposite edges (i.e., top and bottom edges) of the stent ring 14 when positioned within a heart valve 10. That is, the upper flange portions 36 will be positioned in the area between adjacent stent posts 16 on the outflow end 24 of the valve structure 12, and the lower flange portions 38 will be positioned generally below the upper flange portions 36, but on the opposite side of the valve structure 12 (i.e., along the bottom edge of the stent ring 14 on the inflow end 22 of the valve structure 12).

Orientation and positioning of the stents of the invention may be accomplished either by self-orientation of the stents (such as by interference between features of the stent and a previously implanted stent or valve structure) or by manual orientation of the stent, such as by manipulation of its delivery system, to align its features with anatomical or previous bioprosthetic features, such as can be accomplished using fluoroscopic visualization techniques, for example. For example, when aligning the stents of the invention with a previously implanted bioprosthetic valve, features of the stents can align with the stent rail and/or commissures of the valve. It is desirable that the stents be locked in place both rotationally and axially.

Referring again to FIG. 1, the length and shape of each of these upper and lower flange portions 36, 38 can be the same or different from each other within a single support structure 31, as desired. The upper and lower flange portions 36, 38 may be generally "U" or "V" shaped, as illustrated, although the distance between opposite "legs" or extending portions of the members will generally be larger than the distance between the legs of the upper and lower vertical members 32, 34 within the same stent 30, particularly when the stent 30 is in its expanded state. Each upper flange portion 36 includes a distal tip 44 and each lower flange member 38 includes a distal tip 46. The tips 44, 46 may have a tighter curvature than the rest of their respective flange portions 36, 38, if desired. The tips 44, 46 may also serve as interfaces or connecting portions with a corresponding delivery system, as will be explained in further detail below.

The lower flange portions 38 are configured to engage with the lower surface of a sewing ring 14 of a previously implanted prosthetic heart valve (e.g., heart valve 10) when the stent 30 is in its expanded condition. Alternatively, the lower flange portions 38 can be configured to engage other structure(s) of the previously implanted prosthetic heart valve. Referring to FIG. 1, in order to engage with a previously implanted heart valve, one exemplary embodiment of a lower flange portion 38 includes a wire structure that extends generally from a common area 42 on one upper vertical member 32 toward the tip 46 of the flange portion 38, then toward another common area 42 on an adjacent upper vertical member 32. The curvature or contours of each flange portion 38 can be designed so that it closely matches the shape of the stent or valve structure 12 in which it will be implanted, such as at its inflow end 22. That is, there is preferably minimal to no gap between the flange 38 and the interior surface of the valve structure 12.

Each of the tips 46 of the flange portions 38 are positioned approximately 120 degrees from each other around the periphery of the sewing ring 14, although they can be spaced differently from each other, depending on the locations of the stent posts of the heart valve. When the stent 30 is in an expanded condition, the lower flange portions 38 are preferably biased toward the sewing ring 14 to keep the flange portion 38 in place relative to the heart valve 10.

The upper flange portions 36 are configured to engage with the spaces between stent posts 16 of a previously implanted heart valve (e.g., heart valve 10) when the stent 30 is in its expanded condition. Alternatively, the upper flange portions 36 can be configured to engage other structure(s) of the previously implanted prosthetic heart valve. In order to engage with a previously implanted heart valve, one exemplary embodiment of an upper flange portion 36 includes a wire structure that extends generally from a common area on one upper vertical member 32 toward the tip 44 of the flange portion 36, then toward another common area on an adjacent vertical member 32. The curvature or contours of each flange portion 36 can be designed to closely match the shape of the stent or valve structure 12 in which it will be implanted. Each of the tips 44 of the flange portions 36 are positioned approximately 120 degrees from each other around the periphery of the sewing ring 14, although they can be spaced differently from each other, depending on the locations of the stent posts of the heart valve. In any case, the tip 44 of flange portion 36 will preferably fit between adjacent stent posts 16 in order to help physically dock or connect the stent 30 to the previously implanted heart valve 10. When the stent 30 is in an expanded condition, the upper flange portions 36 are preferably biased toward the sewing ring 14 (and preferably toward a corresponding lower flange portion 38) to keep each flange portion 36 in place relative to the heart valve 10.

The support structure 31 of the stent 30 is, in one embodiment, a wire stent capable of transitioning from a collapsed state to an expanded state, where a number of individual wires comprising the support structure 31 are formed of a metal or other material. These wires are arranged in such a way that a support structure 31 is provided that allows for folding or compressing to a contracted state in which its internal diameter is at least somewhat smaller than its internal diameter in an expanded state. In its contracted state, such a support structure 31 with attached valves can be mounted relative to a delivery device, and the support structure 31 is configured so that it can be changed to its expanded state when desired. The delivery systems of the invention used for such replacement heart valve can optionally be provided with degrees of rotational and axial orientation capabilities in order to properly position the new heart valve within the previously implanted heart valve.

The wires of the support structure 31 can alternatively be formed from a shape memory material such as a nickel titanium alloy (e.g., Nitinol). With this configuration, the support structure 31 is self-expandable from a contracted state to an expanded state, such as by the application of heat, energy, and the like, or by the removal of external forces (e.g., compressive forces), such as external forces provided by the delivery system. In addition, the support structure 31 of this embodiment may be laser cut from a single piece of material or may be assembled from a number of different components. For these types of stent structures, one example of a delivery system that can be used includes a catheter with a retractable sheath that covers a compressed stent (thereby providing external compressive forces on the stent) until it is to be deployed, at which point the sheath can be retracted to allow the stent to expand.

The support structure 31 can include features not specifically described or shown instead of, or in addition to, the various coupling structures and methods described herein. For example, the support structure 31 can have a non-expandable design, but can instead be sized and shaped to nest within a previously implanted heart valve (not shown) in a manner that presses features of the previously implanted heart valve (e.g., leaflets) outwardly relative to the native conduit.

The height and diameter of the stent 30 in its expanded state is preferably chosen and/or designed for use with a previously implanted prosthetic heart valve having a particular size and shape. Thus, the stent 30 can assume a variety of different longitudinal heights and/or diameters. In one embodiment, for example, the support structure 31 has a height in its expanded state that is slightly greater than a height of the previously implanted prosthetic heart valve, and/or has a freestanding outer diameter that is greater than an inner diameter of the previously implanted prosthetic heart valve. With this embodiment, upon transitioning toward the expanded state, the support structure 31 (including the vertical members 32, 34) presses against an inner diameter of the previously implanted prosthetic heart valve. The overall shape of the support structure 31 is cylindrical in many cases; however, other shapes are also contemplated, such as elliptical, oval, or the like. For example, portions of the support structure 31 can define an enlarged diameter as compared to other portions. Further, depending upon the previously implanted heart valve being functionally replaced, the support structure 31 can be less uniform along a height thereof.

Figure 27:
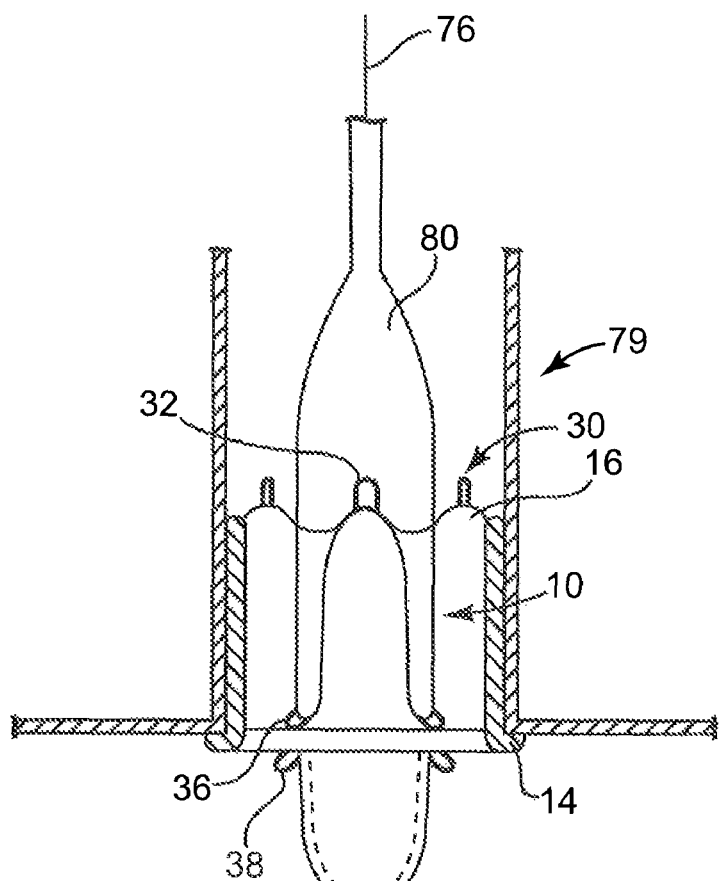
FIG. 27 is a partial-cross sectional side view of one embodiment of a delivery system for implanting a balloon-expandable stent.

One method of delivering a stent (e.g., stent 30) to the location of a previously implanted heart valve (e.g., heart valve 10) is performed percutaneously, as represented in simplified form in FIG. 27. In general terms for this exemplary delivery system, a transcatheter assembly 70 is provided, including a delivery catheter 72, a balloon catheter 74, and a guide wire 76. The delivery catheter 72 is of a type known in the art, and defines a lumen 78 within which the balloon catheter 74 is received. The balloon catheter 74, in turn, defines a lumen (not shown) within which the guide wire 76 is slidably disposed. Further, the balloon catheter 74 includes a balloon 80 that is fluidly connected to an inflation source (not shown). It is noted that if the stent being implanted is a self-expanding type of stent, the balloon would not be needed and a sheath or other restraining means would instead be used for maintaining the stent in its compressed state until deployment of the stent. In any case, in this embodiment, the transcatheter assembly 70 is appropriately sized for a desired percutaneous approach to the prosthetic heart valve 10 that was previously implanted in a native heart valve 79. For example, the transcatheter assembly 70 can be sized for delivery to the heart valve 10 via an opening at a carotid artery, a jugular vein, a sub-clavian vein, femoral artery or vein, or the like. Essentially, any percutaneous intercostals penetration can be made to facilitate use of the transcatheter assembly 70.

Prior to delivery, the stent 30 is mounted over the balloon 80 in a contracted state to be as small as possible without causing permanent deformation of the stent structure. As compared to the expanded state, the support structure 31 is compressed onto itself and the balloon 80, thus defining a decreased inner diameter as compared to an inner diameter in the expanded state. Further, the vertical members 32, 34 and flange portions 36, 38 are compressed toward the longitudinal axis 40 when in the contracted state. While this description is related to the delivery of a balloon-expandable stent, the same basic procedures can also be applicable to a self-expanding stent, where the delivery system would not include a balloon, but would preferably include a sheath or some other type of configuration for maintaining the stent in its compressed condition until its deployment.

With the stent 30 mounted to the balloon 80, the transcatheter assembly 70 is delivered through a percutaneous opening (not shown) in the patient via the delivery catheter 72. The previously implanted heart valve 10 is located by inserting the guide wire 76 into the patient, which guide wire 76 extends from a distal end 82 of the delivery catheter 72, with the balloon catheter 74 otherwise retracted within the delivery catheter 72. Once the previously implanted heart valve 10 has been located, the balloon catheter 74 is advanced distally from the delivery catheter 72 along the guide wire 76, with the balloon 80 and stent 30 positioned relative to the previously implanted heart valve 10. More particularly, the balloon 80 and stent 30 are positioned within the internal region of the previously implanted prosthetic heart valve 10, with the lower flange portions 38 positioned adjacent the sewing ring 14 of the heart valve 10, and the upper flange portions 36 are positioned adjacent the outflow end 24 of the previously implanted prosthetic heart valve 10.

With a stent in its contracted state, its support structure can readily move within the internal area of the previously implanted prosthetic heart valve, and any vertical members and flange portions, which are otherwise retracted or compressed, do not unintentionally contact or engage portions of the previously implanted prosthetic heart valve. In one embodiment, the stent includes a radiopaque, echogenic, or MRI visible material to facilitate visual confirmation of proper placement of the stent relative to the previously implanted prosthetic heart valve. Alternatively, other known surgical visual aids can be incorporated into the stent.

The techniques described above relative to placement of the stent within the heart can be used both to monitor and correct the placement of the stent in a longitudinal direction relative to the length of the anatomical structure in which it is positioned and also to monitor and correct the orientation of the stent relative to the stent posts 16 of the previously implanted heart valve. In particular, it is desirable for the stent to be positioned so that each of its upper flange portions are between two adjacent stent posts when they are expanded outwardly.

Once the stent is properly positioned, the balloon catheter 74 is operated to inflate the balloon 80, thus transitioning the stent to the expanded state, such as is shown in FIG. 1 relative to stent 30. Alternatively, if the support structure is formed of a shape memory material, the stent can be allowed to self-expand to the expanded state of FIG. 1. Thus, a self-expanding stent structure can be percutaneously delivered by an appropriate catheter device other than a balloon catheter, as will be described in further detail below. In either case, the support structure expands within the internal region 20 of the previously implanted heart valve 10, radially pressing against the valve structure 12. Because the previously implanted prosthetic heart valve 10 would have included leaflets (not shown), radial expansion of the stent would press against these leaflets, thereby lodging them against the valve structure 12.

Figure 28:
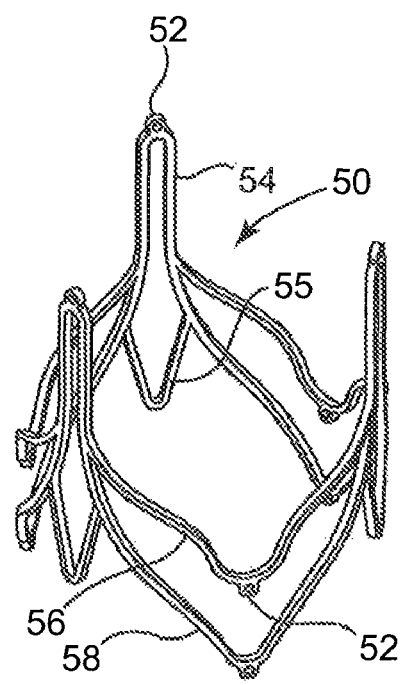
FIG. 28 is a perspective view of another stent embodiment as it can be used as a component of a replacement heart valve.

FIG. 28 illustrates an embodiment of another exemplary stent 50 that includes a number of eyelets or apertures 52 that can be used for maintaining the various components of stent 50 in a compressed state when desired. These eyelets 52 can be particularly useful in the case where the stent 50 is a self-expanding stent, since this type of structure needs external forces to keep it in its compressed state. In particular, an eyelet 52 may be located at the end of at least one of the multiple upper vertical members 54 and/or one or more of the upper and lower flange portions 56, 58 and the lower vertical members 55. Each eyelet 52 is preferably sized for accepting an elongated thread-like material, such as suture material or a thin wire, and/or sized for engagement with a hook or other engagement feature of a delivery device. If a thread-like material is used, it can be threaded through at least one of the eyelets 52 in such a way that when the material is pulled tight, the eyelets 52 are pulled toward the central axis of the stent 50. If a wire-like material is used, it may be configured as a metal snare or other configuration that pulls the eyelets 52 toward the central axis of the stent 50. If a delivery device having such engagement features is used, it may be configured in such a way that the engagement features can be moved toward and away from the central axis of the stent, as desired for insertion and deployment of the stent.

Other arrangements of pulling the various portions of a stent toward a central stent axis are also contemplated, which preferably are relatively easy to operate for compression and release of the stent structures. In any case, once the stent structure is compressed to its desired configuration, the feature used to pull the stent into its compressed configuration is capable of being secured or fastened in some way to keep the stent from unintentionally expanding. This same feature can have its operation reversed to allow the various structures of the stent to move toward their expanded state.

FIGS. 29-32 illustrate one exemplary system of delivering a stent of the type illustrated in FIG. 28, for example, into a heart valve 10, which would have previously been implanted in a patient. One feature provided by the delivery system of this embodiment is that it allows a self-expanding stent to be retrieved after its initial deployment if it is not positioned correctly in the heart. The stent then could be redeployed into the proper position, using the same or a different delivery system. With particular reference to the Figures, a distal portion of a delivery system 90 is illustrated, which includes a tip portion 92 and a sheath 94. The system further includes a plurality of hooks or engagement features 96 that can engage with eyelets 52 of stent 50, for example. While this delivery system 90 can generally be used for more procedures than the described implantation procedure, the procedure illustrated relative to FIGS. 29-32 is particularly directed to percutaneous delivery of a stent to a previously implanted aortic heart valve via a retrograde approach. For purposes of this description of an implantation method, the exemplary stent 50 of FIG. 28 is used in the implantation description; however, a number of different stent embodiments may utilize these same procedures, such as other stent embodiments described herein.

Figure 29:
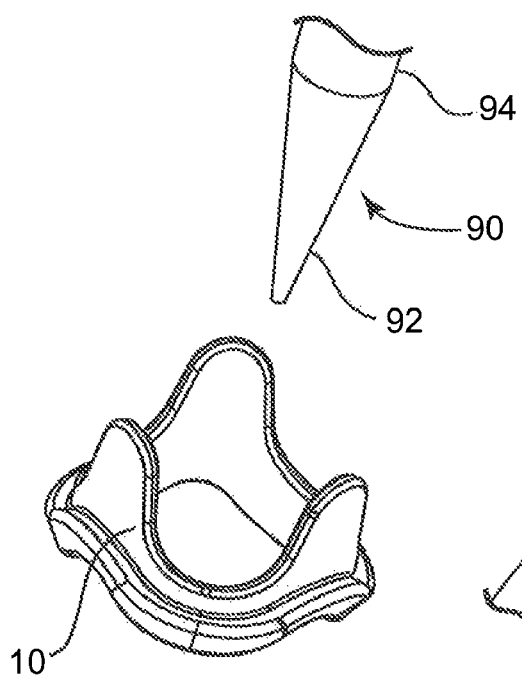
FIGS. 29-32 are sequential perspective views of the implantation of a self-expanding stent in a prosthetic heart valve, utilizing a retrograde approach of implantation.

As illustrated in FIG. 29, delivery system 90 is being advanced toward heart valve 10 as such a heart valve would have been previously implanted in a patient. The compressed replacement valve (not shown) is encompassed within sheath 94 for insertion into the patient so that there is no contact between the replacement valve and any portion of the patient's internal anatomy during the insertion process.

Figure 30:
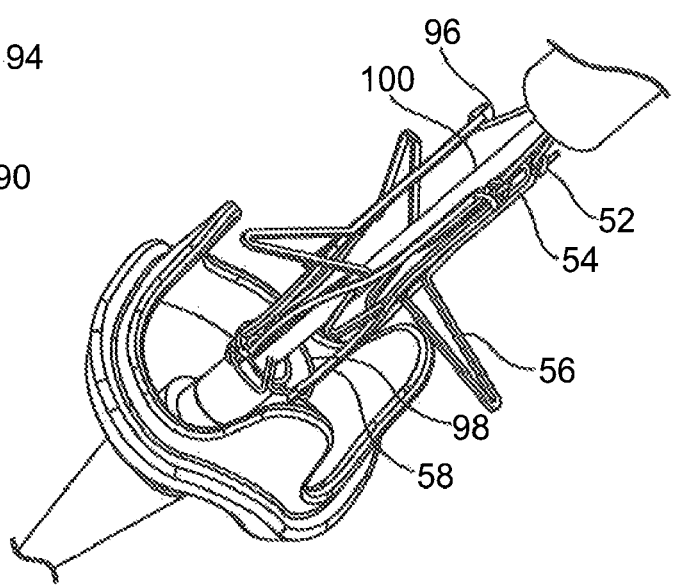

FIG. 30 illustrates delivery system 90 as it has been further advanced into heart valve 10, and wherein the sheath 94 has been partially retracted away from the tip 92 to expose a portion of the stent 50 that was previously compressed therein. Because the upper flange portions 56 are no longer constrained by the sheath 94, these portions 56 are able to move away from a central member 100 of the delivery system 90 as the sheath 94 is retracted. Further, eyelets 52 that extend from the ends of upper vertical members 54 are each engaged with a hook 96 of the delivery system 90. These hooks 96 can be attached to a mechanism within the interior portion of the sheath 94, for example, or may be attached to some other structure that extends through the sheath 94. In either case, hooks 96 can maintain the upper vertical members 54 in their compressed state until they are disengaged from the hooks 96. That is, the delivery system can control the diameter of the stent inflow structures, the stent outflow structures, or both the stent inflow and outflow structures independently or together. As is also illustrated in FIG. 30, the lower flange portions 58 are held in their compressed state with a snare 98 that engages with eyelets 52 that extend from each of the flange portions 58. Snare 98 is shown as a single, shaped piece of elongated material; however, the lower flange portions 58 may instead be held in their compressed state via an alternative structure or system, such as by a suture, or by a moveable sleeve attached to the delivery system, for example.

Figure 31:
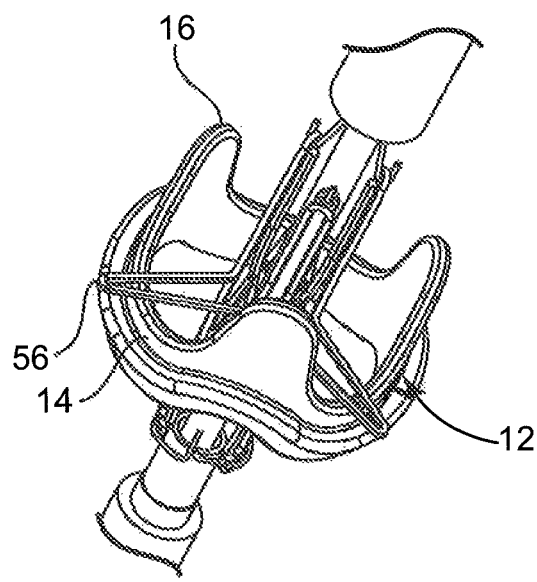

As shown in FIG. 31, the delivery system 90 is further advanced into valve 10 until the upper flange portions 56, which are extending radially away from the central member 100 of the delivery system 90, become engaged with the valve structure 12 of the heart valve 10. In particular, each of the upper flange portions 56 are preferably positioned to be in contact with the surface of the stent ring 14 between two adjacent stent posts 16. In order to verify that the flange portions 56 are properly positioned relative to the valve structure 12 (e.g., flange portions 56 are not resting on the top of the stent posts 16), the entire delivery system 90 can be rotated slightly in either direction while pressing downwardly toward the valve structure 12. The system 90 can also be advanced axially to the desired position. In this way, the flange portions 56 can be moved into the area between adjacent stent posts 16 if they are not already in this position.

Figure 32:
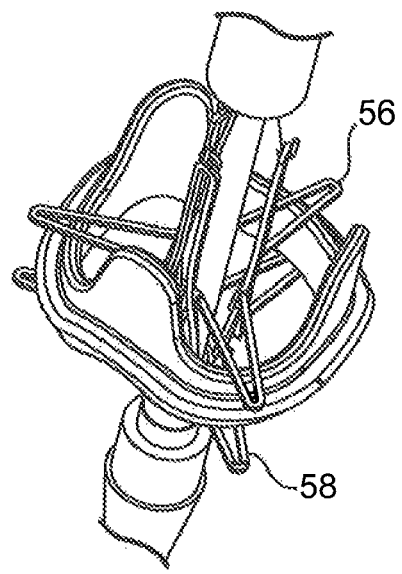

Once the delivery system 90 and its stent 50 are properly oriented, the snare 98, sheath, or other structure holding the lower flange portions 58 in their compressed state is released or retracted, thereby allowing the lower flange portions 58 to deploy or radially extend, as illustrated in FIG. 32. The lower flange portions 58 can then contact the surface of the stent ring 14 that is opposite the surface that is contacted by the upper flange portions 56. The hooks 96 can then be disengaged from the eyelets 52 of stent 50, such as by further advancing the delivery system 90 into the opening of the valve 10, or by activating a mechanism associated with the hooks 96 that can move the hooks 96 relative to the eyelets 52 until they become disengaged from the eyelets 52. It is noted that the stent is retrievable at any point prior to the hooks 96 being disengaged from the stent 50 with use of the hooks 96 and/or the sheath 94. The upper and lower vertical members 54, 55 are then free to expand radially until they contact the inner surface of the stent or valve structure 12. The upper and lower vertical members 54, 55 preferably are configured so that they will press against the inner surface of the valve structure 12 with sufficient force to provide further anchoring of the stent 50 within the previously implanted heart valve 10.

After the stent 50 is implanted and its various portions are deployed or released from a compressed state to an expanded state, the delivery system 90 can be removed from the patient. The stent 50 will then be in its deployed or expanded state, as is generally illustrated in FIG. 28, or in a similar manner to that illustrated in FIG. 1 relative to a stent 30.

FIG. 2 illustrates another exemplary embodiment of a stent 110 that has a similar structure to the stent 30 of FIG. 1, but further includes at least one stent post engaging structure 112. Relative to the specific embodiment of the stent 110 that is illustrated, this structure also does not include upper flange portions (such as upper flange portions 36 of stent 30), since such portions could be redundant and/or interfere with the specific structure of the structures 112 shown. However, it is contemplated that upper flange portions could also be provided with this embodiment, if they are configured to not interfere with any stent post engagement structures 112. Further, in the embodiment shown in this figure, three structures 112 are provided to correspond with a like number of stent posts 16 of heart valve 10; however it is contemplated that the stent 110 includes less than three structures 112, even if three stent posts are provided. If less than three structures 112 are provided, it may be desirable to additionally provide at least one upper flange portion to engage with the heart valve 10.

Each stent post engaging structure 112 is configured to partially surround a portion of a stent post 16, thereby providing another way of anchoring the stent 110 in place. These structures 112 can cooperate with one or more lower flange portions 114 to provide anchoring on both the inflow and outflow ends of the previously implanted heart valve 10. The structures 112 can be individual structures that are each secured to upper vertical members 116, or may be formed as a single structure having multiple loops that are secured to the structure of the stent 110. Alternatively, these structures 112 can be integrally formed with the structure of the stent 110. Stent 110 can be a self-expanding stent or may be a balloon-expandable stent structure.

FIGS. 3-5 illustrate another exemplary embodiment of a stent 120 for use with a replacement prosthetic heart valve in accordance with the present invention. Stent 120 includes a number of strut or wire portions arranged relative to each other to provide secure coupling between the stent 120 and a previously-implanted prosthetic heart valve, such as heart valve 10. In addition, stent 120 provides a semi-rigid frame for the leaflets of the replacement heart valve, which will be attached to the interior portion of stent 120, as will be described in further detail below.

Stent 120 includes multiple upper vertical members 122 spaced apart from each other around the perimeter of the stent 120, and a corresponding number of lower vertical members 124. It is understood that the number of upper and lower vertical members can be different from each other, however. Both the upper and lower vertical members 122, 124 extend in a direction that is generally parallel to a longitudinal axis of the stent 120, thereby partially defining the generally cylindrical shape of the stent 120. Upper vertical members 122 extend generally toward the outflow end of the stent structure 12, and the lower vertical members 124 extend in a direction that is generally opposite to the direction of the upper vertical members 122, which is toward the inflow end of the stent structure 12. As with previously described embodiments, the number of upper and lower vertical members 122, 124 may or may not be the same as the number of stent posts of the stent structure 12. In addition, the length of upper and lower vertical members 122, 124 should be adequate to provide sufficient contact between the stent 120 and the stent structure 12 to help keep the stent 120 in place relative to the heart valve 10.

Stent 120 further includes upper and lower flange portions 126, 128, respectively. Flange portions 126, 128 are configured for positioning on opposite sides of a stent ring 14 of stent structure 12 when the stent is in its expanded state. Through the design and manufacturing of the stent 120, the flange portions 126, 128 can be biased toward each other when the stent is in its expanded condition in order to keep the stent 120 positioned properly relative to a stent structure 12.

Stent 120 includes components that can be made of materials that perform differently relative to deployment thereof. In particular, a portion of stent 120 can be expandable from its compressed state via the application of an internal radial force (e.g., inflation of a balloon), while another portion of stent 120 can be self-expandable such that the removal of radial compressive forces will allow that portion of stent 120 to expand without application of additional forces. Alternatively, different portions of the stent 120 can be made of different materials that are both self-expanding, or of different materials that are expandable via the application of an internal radial force. Although the components that comprise these two structures can vary, the stent 120 illustrated in FIGS. 3-5 includes a first component that is expandable through application of a radial force. This component may be made of a material such as stainless steel, for example. The first component includes the upper vertical members 122, lower vertical members 124, and lower flange portions 128, and can include a number of components attached to each other, or can be a single machined piece. This first component is illustrated in its compressed state in FIG. 3 and in its expanded state in FIGS. 4 and 5. The stent 120 further includes a second component that is self-expandable and may be made of a shape memory material such as a nickel titanium alloy (e.g., Nitinol). This second component includes the upper flange portions 126 and also a second lower vertical member 130 that can at least roughly duplicate the shape of the lower vertical member 124 of the first component.

When this stent 120 is implanted into a patient, a sheath or other mechanism of its delivery system will hold the self-expandable portions of the stent in a compressed state until such a mechanism is retracted or removed, thereby allowing the upper flange portions 126 to extend radially from the stent structure, as is illustrated in FIG. 3. These upper flange portions 126 are preferably positionable between adjacent stent posts of a previously implanted heart valve for proper orientation of the stent 120. Because the first component is not made from a self-expandable material, the first component of stent 120 will remain in its compressed state, as shown in FIG. 3, until it is expanded radially, such as via expansion by a balloon catheter that is positioned in its central opening. When fully inflated, such a balloon will be constrained by the stent structure 12 along a portion of its length, but portions of the balloon that are above and below the stent structure 12 can be allowed to expand further so that the balloon takes on an "hourglass" type of shape, thereby pressing the lower flange portions 128 outward and under the stent ring 14, as illustrated in FIG. 5. These lower flange portions 128 can thereby help to anchor the stent 120 relative to the heart valve in which it is positioned. Thus, FIG. 5 illustrates the stent 120 in its expanded state, where the upper and lower flange portions 126, 128 are positioned on opposite sides of stent ring 14, and where the vertical members 122, 124, 130 are positioned adjacent to the internal portion of stent structure 12.

FIG. 6 illustrates another exemplary embodiment of a stent 140 for use as a replacement prosthetic heart valve in accordance with the invention. This stent 140 includes similar structures to those of the stent 30 of FIG. 1; however, stent 140 does not include lower vertical members that correspond to and extend in the opposite direction from upper vertical members 142. Otherwise, stent 140 can include any of the features described herein. Stent 140 can be self-expanding or expandable with application of a radial force, and pericardial tissue or other materials may be attached to its structure to provide a prosthetic heart valve.

Figure 7:
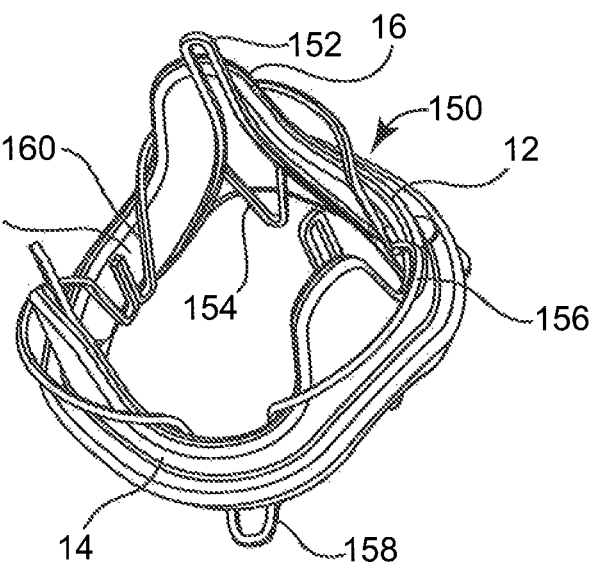
FIG. 7 is a perspective view of another exemplary embodiment of a stent of a replacement valve positioned within a prosthetic heart valve.

FIG. 7 illustrates another exemplary embodiment of a stent 150 for use as a replacement prosthetic heart valve in accordance with the present invention. Stent 150 includes similar structures to the stent 110 of FIG. 2, including upper vertical members 152 and corresponding lower vertical members 154, stent post engagement structures 156, and lower flange members 158. In an embodiment where the number of stent post engagement structures 156 is optionally less than the number of corresponding stent posts of the previously implanted heart valve, upper flange members may be included on stent 150, if desired. Alternatively, upper flange members may be included on stent 150 in a configuration that does not interfere with the structures 156.

Stent 150 further includes "W" shaped structures 160 positioned along the stent ring 14 between adjacent stent posts 16 in the interior area of the stent structure 12. Each structure 160 is positioned generally between adjacent lower flange members 158 and provides additional contact surfaces between the stent 150 and the interior portion of the stent structure 12. In addition, any or all of the structures 160 can be used to hold a leaflet of the failed bioprosthesis against the stent ring of the failed bioprosthesis (such as stent ring 14) so that the leaflets of the failed bioprosthesis do not interfere with the valve leaflets of the newly implanted valved stent. That is, it may be desirable to hold the leaflets of the failed bioprosthesis toward the stent ring in order to minimize the potential for formation of thrombus between the failed leaflets and the new leaflets. In addition, holding the leaflets against the stent ring can prevent abrasion and/or tearing of the new leaflets that can occur during repeated contact with the old leaflets. The structures 160 may take a "W" type shape, as shown, or may instead have a different shape, such as one or more "U" or "V" shapes, a series of extensions, a sinusoidal shape, or any desired configuration that can hold leaflets against the stent ring of the failed bioprosthesis, when desired.

The stent 150 may comprise any desired number of components that are connected or attached to each other; however, the exemplary embodiment of stent 150 illustrated in FIG. 7 provides an embodiment with two separate structures attached or arranged relative to each other. That is, a first component is a formed structure that includes the stent post engagement structures 156 and the "W" shaped structures 160, while a second component is a formed structure that includes the upper and lower vertical members 152, 154 and the lower flange members 158.

Figure 8:
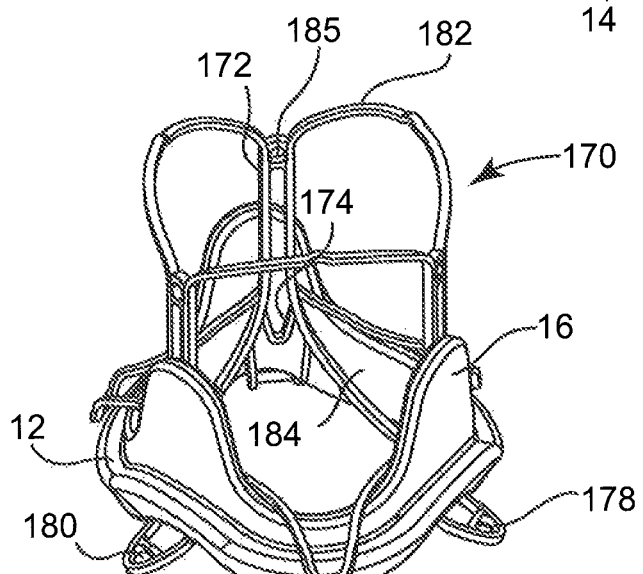
FIG. 8 is a perspective view of another exemplary embodiment of a stent of a replacement valve positioned within a prosthetic heart valve.

FIG. 8 illustrates another exemplary embodiment of a stent 170 for use as a prosthetic heart valve in accordance with the present invention. Stent 170 generally includes upper vertical members 172 and corresponding lower vertical members 174, upper flange members 176, lower flange members 178, and upper connecting members 182. In this embodiment, the upper flange members 176 are offset relative to lower flange members 178 such that each of the upper flange members 176 is positioned generally between adjacent stent posts 16 of stent structure 12, and each of the lower flange members 178 is generally aligned with the stent posts 16. Upper connecting members 182 extend between adjacent upper vertical members 172 and are provided for tying together the upper vertical members 172 to carry the valve hydrodynamic closing loads, which can thereby reduce various stresses in the stent. The upper connecting members 182 can also provide interface points for connection of the stent 170 with the delivery system used for the implantation process. Stent 170 further includes optional lower connecting members 184 that extend between adjacent lower vertical members 174. Lower connecting members 184 are provided for attachment of the material that makes up the leaflets of the replacement heart valve. That is, pericardial or another valve material may be sewn or otherwise attached to the lower connecting members 184 and may further be sewn or otherwise attached to the upper vertical members 172.

The upper connecting members 182 are shown as a single curved member; however, the connecting members can have any desired structure or configuration that provides the desired support for the upper vertical members 172. Further, the connecting members 182 may be made of the same or a different material than the other portions of the stent.

One or more of the lower flange members 178 may further include an eyelet or aperture 180 for engagement with a structure of a delivery system for use during the implantation of the stent 170 (e.g., sutures or a hook structure that can pull the stent structure toward its central axis). One or more of the upper vertical members 172 may similarly include an eyelet or aperture 185 for use during the implantation of the stent 170 and/or for use as an anchor point for attachment of valve material to the stent 170.

Figure 9:
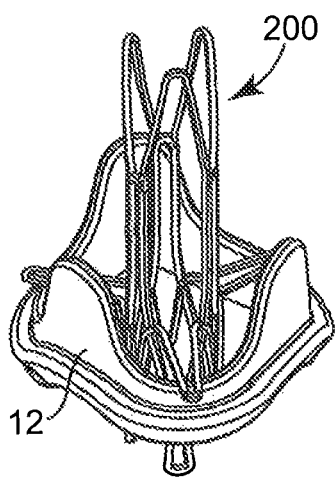
FIG. 9 is a perspective view of another exemplary embodiment of a stent of a replacement valve positioned within a prosthetic heart valve, with the stent in its partially compressed state.
Figure 10:
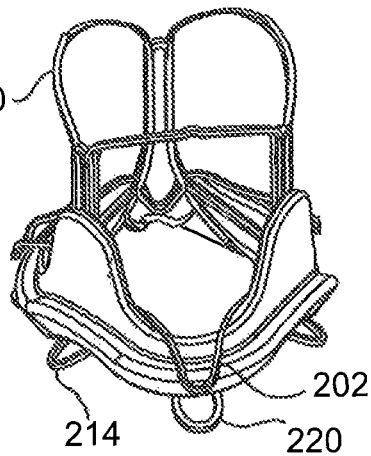
FIG. 10 is a perspective view of the stent of FIG. 9 positioned within a prosthetic heart valve, with the stent in its expanded state.
Figure 11:
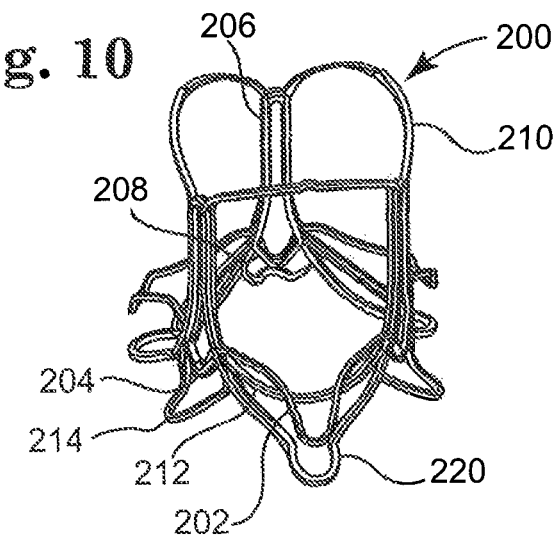
FIG. 11 is a perspective view of the stent of FIG. 10.

FIGS. 9-11 illustrate another exemplary embodiment of a stent 200 for use as a replacement prosthetic heart valve in accordance with the present invention. Stent 200 is similar to stent 120 of FIGS. 3-5 in that stent 200 also includes a portion that is made of a material that is expandable (e.g., stainless steel) with a device such as a balloon catheter, for example, and a portion that is made of a material that is self-expanding (e.g., Nitinol) when external forces are removed. In particular, a self-expanding portion of stent 200 may include upper flange portions 202 that can be generally positioned between adjacent stent posts 16 of a stent structure 12, and bracing portions 204 that can be generally aligned with stent posts 16 of a stent structure 12. The other portion (i.e., the portion that is not self-expanding) of the stent 200 may include any or all of the following structures: upper vertical members 206; lower vertical members 208; upper support structures 210 extending between adjacent upper vertical members 206; lower support structures 212 extending between adjacent lower vertical members 208, lower flange portions 220; and intermediate lower flange portions 214 located between adjacent lower flange portions 220. The lower flange portions 214 can provide additional anchoring force for the stent 200 against the stent structure 12 in the areas generally adjacent to the stent posts 16. The lower support structures 212 may be used for securing the valve structure to the stent 200, if desired.

Figure 12:
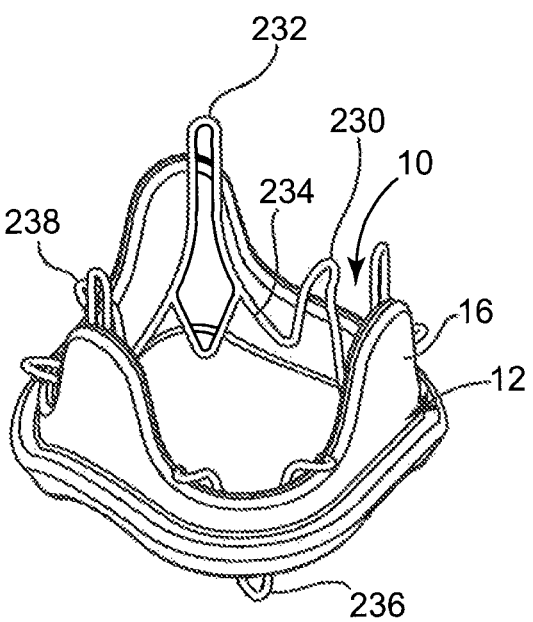
FIG. 12 is a perspective view of another exemplary embodiment of a stent of a replacement valve positioned within a prosthetic heart valve.

FIG. 12 illustrates another exemplary embodiment of a stent 230 for use as a prosthetic heart valve. Stent 230 includes multiple upper vertical members 232 and optional corresponding lower vertical members 234, and multiple lower flange members 236. The number of upper vertical members 232 and lower vertical members 234 preferably correspond to the number of stent posts of the previously implanted heart valve. In addition, the number of lower flange members 236 preferably corresponds to the number of stent posts 16 of the previously implanted heart valve 10 so that one lower flange member 236 can be positioned generally between two adjacent stent posts 16, but on the opposite side of the stent structure 12 from the stent posts 16. The stent 230 further includes multiple upper flange members 238, which are positionable in the space between every two adjacent stent posts 16, but on the same side of the stent structure 12 as the stent posts 16. In this embodiment, two upper flange members 238 are positioned in each of the spaces between two adjacent stent posts 16, which thereby provide additional anchoring points for the stent 230 within the stent structure 12. In addition, these flange members 238 can function similarly to the structures 160 described above relative to FIG. 7 in that one or more of the flange members 238 can help to hold the leaflets of the failed bioprosthesis generally against the stent ring of the bioprosthesis so that they do not interfere with the leaflets of the new valved stent. The stent 230 can be configured so that each of the upper flange members 238 of the pair of upper flange members are angled at least slightly toward their adjacent stent posts 16 so that they are facing in at least slightly opposite directions from each other.

Figure 13:
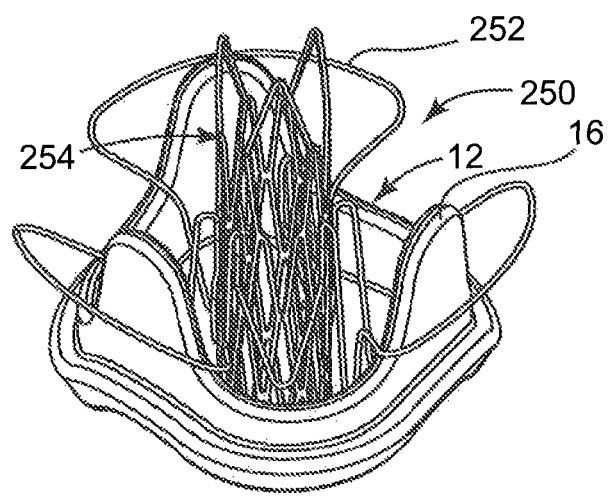
FIG. 13 is a perspective view of another exemplary embodiment of a stent of a replacement valve positioned within a prosthetic heart valve, with the stent in its partially compressed state.
Figure 14:
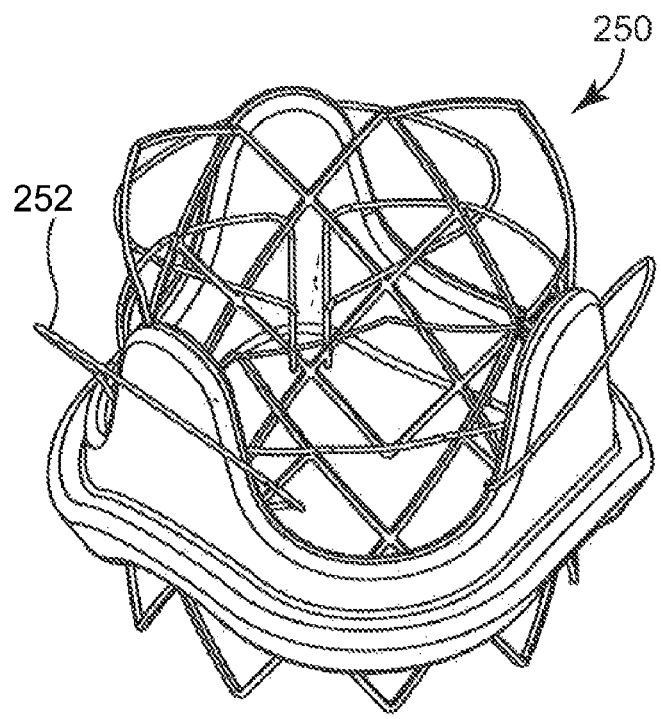
FIG. 14 is a perspective view of the stent of FIG. 13 in its expanded state as positioned within a prosthetic heart valve.

FIGS. 13 and 14 illustrate another exemplary embodiment of a stent 250 for use as a prosthetic heart valve. Stent 250 is similar to stent 120 of FIGS. 3-5 in that stent 250 also includes a portion that is made of an expandable material (e.g., stainless steel) with a balloon catheter, for example, and a portion that is made of a material that is self-expanding (e.g., Nitinol) when external forces are removed. In particular, a self-expanding portion of stent 250 may include multiple stent post engagement structures 252, which are shown in this embodiment as being part of a continuous unit or piece that is configured to include three stent post engagement structures 252. Each of the structures 252 is provided to engage with a stent post 16 of a stent structure 12. The other portion (i.e., the portion that is not self-expanding) of the stent 250 comprises a mesh-like stent structure 254 that includes a number of wire portions arranged as best illustrated in the expanded version of the stent 250 in FIG. 14. Although this embodiment does not illustrate particular flange portions that extend above or below the stent structure 12, it is contemplated that any of the anchoring structures discussed above may be incorporated into the stent 250 to provide additional anchoring mechanisms for the stent 250.

Figure 15:
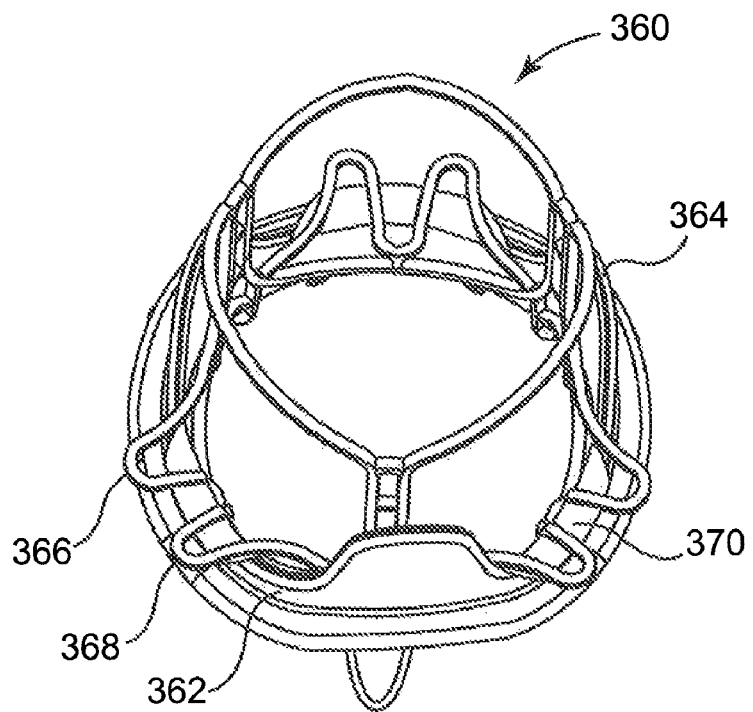
FIG. 15 is a perspective view of a prosthetic heart valve with a stent of a replacement prosthetic heart valve positioned therein and showing the leaflets of the original prosthetic heart valve.

FIG. 15 illustrates another stent 360 of the invention as it can be implanted within a previously implanted heart valve, such as a heart valve 362, and specifically illustrates an exemplary positioning of the leaflets 370 of the previously implanted heart valve 362. Stent 360 includes a split petal structure for its upper flange member that is positioned between stent posts 364, as shown with petals 366, 368. These petals 366, 368 provide two structures for holding the leaflets 370 of the heart valve 362 against the stent rail of that heart valve 362 so that the leaflets 370 do not interfere with the implantation and/or functioning of the newly implanted heart valve. The petals 366, 368 may have the same configuration as each other, as shown, or may instead be differently sized and/or shaped than each other. It is also contemplated that other structures may be used, such as a series of barbs or extending members, and it is further understood that more or less than two structures can be used for holding the leaflets 370 against the rail of the heart valve 362. The petal structures could also be used to hold native leaflets outward for the stented valve implanted in a native valve.

Figure 16:
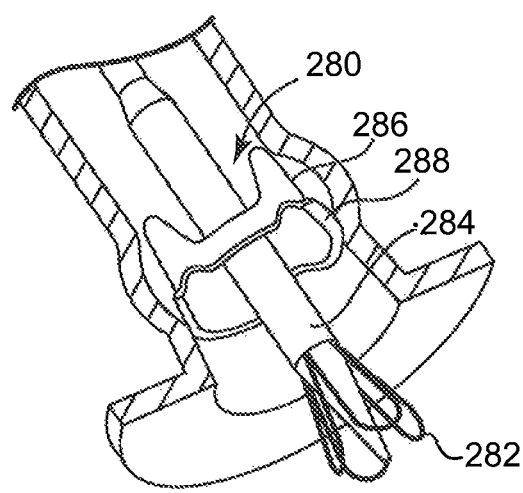
FIG. 16 is a partially cutaway perspective view of a delivery system of the invention positioned relative to a prosthetic heart valve in a heart vessel, with petals of the delivery system in an undeployed state.
Figure 17:
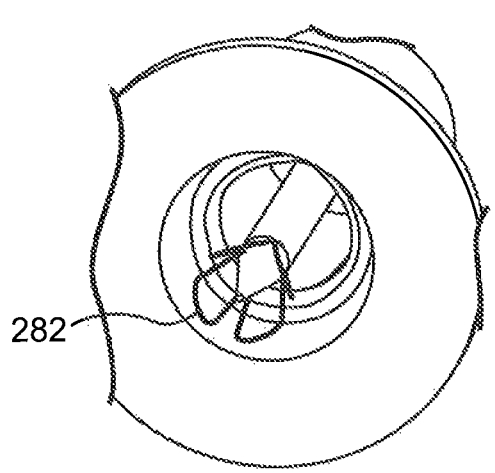
FIG. 17 is a bottom perspective view of the delivery system of FIG. 16.

FIG. 16 is a partial cutaway perspective view of an exemplary delivery system 280 of delivering stents to an area of a failed prosthetic heart valve, and FIG. 17 is a bottom perspective view of the same system. Both of these figures show a series of inflow petals 282 of the delivery system as partially protruding from a sheath 284, with the ends of the petals 282 generally facing the distal end of the delivery system 280. This may be considered to be the undeployed or partially deployed condition of these petals 282, which in this case, includes four petals 282, although a delivery system with more or less petals could alternatively be used. In any case, the delivery system 280 is inserted into the patient until it has passed through a previously implanted heart valve 286 and the petals 282 are positioned adjacent the stent ring 288 of the heart valve 286. The petals 282 are preferably made of a shape memory material such as a nickel titanium alloy (e.g., Nitinol or the like) so that when it is desired to deploy them, the sheath 284 can be retracted a sufficient amount to further expose the petals 282 until the petals 282 tend to move to face generally in the opposite direction from when they are in their undeployed condition. In other words, the ends of the petals 282 will be facing generally away from the distal end of the delivery system 280. That is, due to the shape memory material of these petals 282, releasing the stent from its sheath will release the external compressive force on the petals, thereby allowing petals 282 to move toward their expanded condition or configuration.

Figure 18:
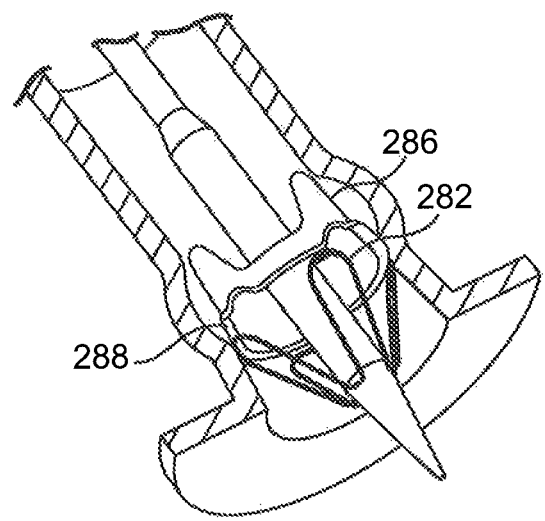
FIG. 18 is a partially cutaway perspective view of the delivery system of FIG. 16 in a further advanced state of delivering of a replacement heart valve.
Figure 19:
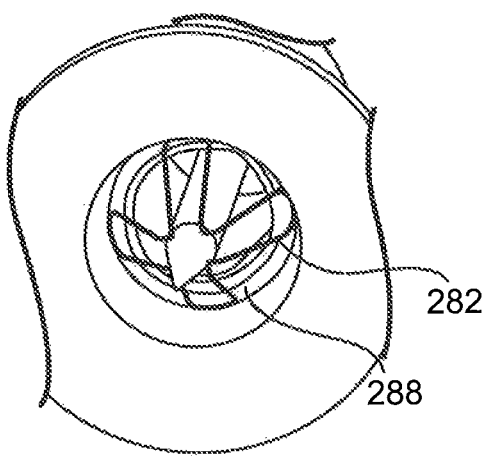
FIG. 19 is a bottom perspective view of the delivery system of FIG. 18.

The entire delivery system 280 can then be retracted until the distal end of the petals 282, which can be spaced at least slightly from the outer surfaces of the delivery system 280, come in contact with the stent ring 288 of the heart valve 286. Alternatively, for the replacement of a native valve, the petals could contact the native valve and/or an adjacent anatomical structure, such as the septum or atrium, depending upon the specific valve anatomy where the stent is being delivered. This position of the delivery system 280 and deployed petals 282 is illustrated in FIGS. 18 and 19. After this deployment of the petals 282 and their engagement with the previously implanted heart valve 286, another sheath can be retracted for deployment of a stent enclosed therein, which stent can include any of the described features and configurations described herein relative to various stent structures and relationships. This delivery system can alternatively be used to deploy stents in a native annulus of a heart valve, if desired, where the deployed petals will be manipulated to contact a structure of the native anatomy rather than the structure of a previously implanted heart valve.

Figure 20:
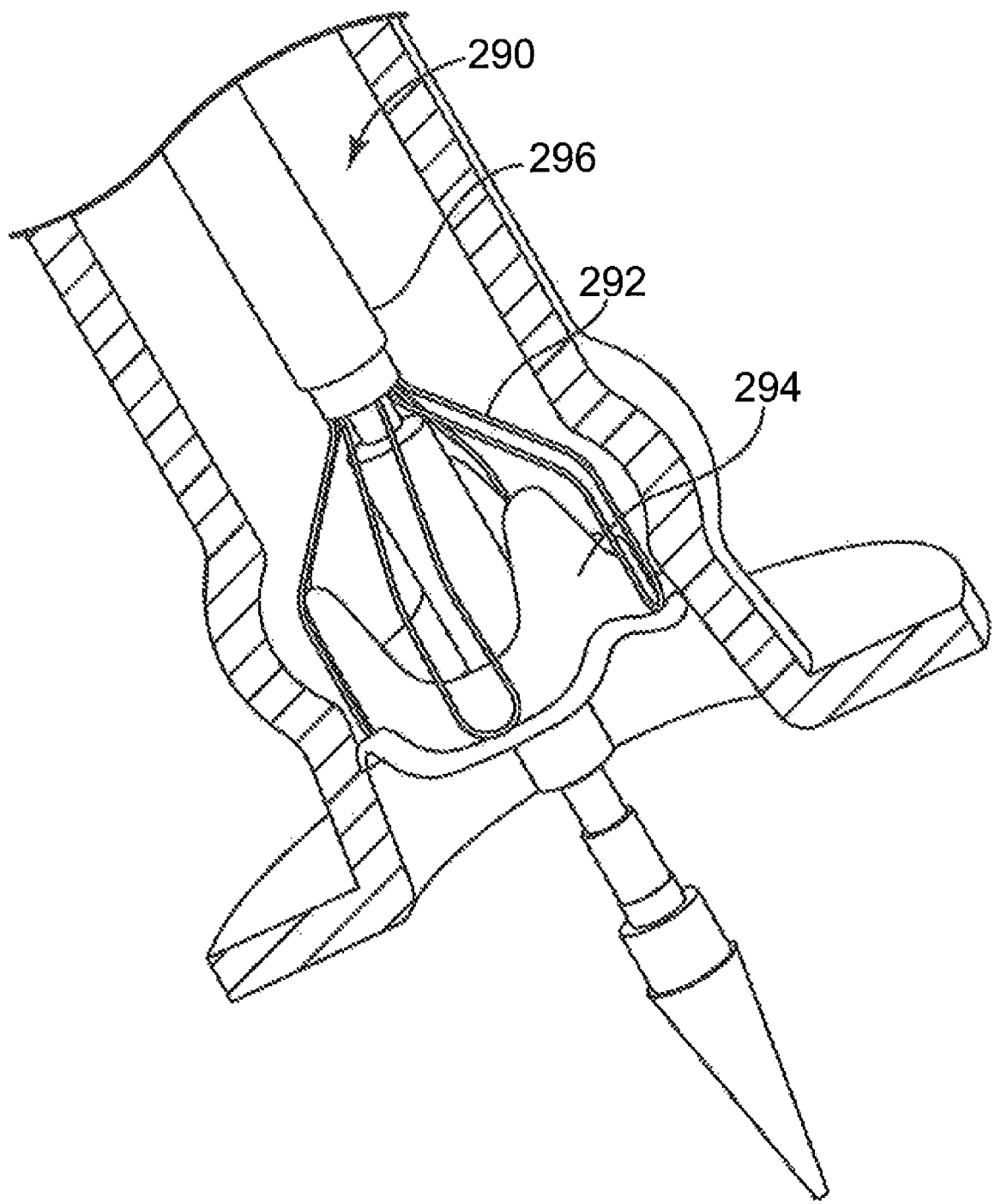
FIG. 20 is a partially cutaway side view of a delivery system positioned in a heart vessel, with delivery system petals interfacing with the outflow of a prosthetic heart valve.

Another delivery system 290 is illustrated in FIG. 20 for delivery of a stent to a previously implanted heart valve 294. Delivery system 290 also includes a sheath 296 that is retractable for deployment of multiple petals 292 of the delivery system. In this embodiment, the petals 292 are deployed to interface with the valve outflow rather than the valve inflow (as described above relative to FIGS. 16-19). Thus, the retraction of the sheath 296 is initiated when the petals 292 are on the outflow side of the heart valve 294. The petals are shown in this Figure as contacting an annulus of the previously implanted heart valve, but could alternatively be configured to contact other parts of the stent frame or leaflets. The petals could similarly be configured to contact the leaflets or annulus of a native valve to facilitate proper positioning of the delivery system and replacement valve prior to valve deployment. The sheath 296 can then be further retracted for full deployment of the stent enclosed therein, when desired.

Figure 21:
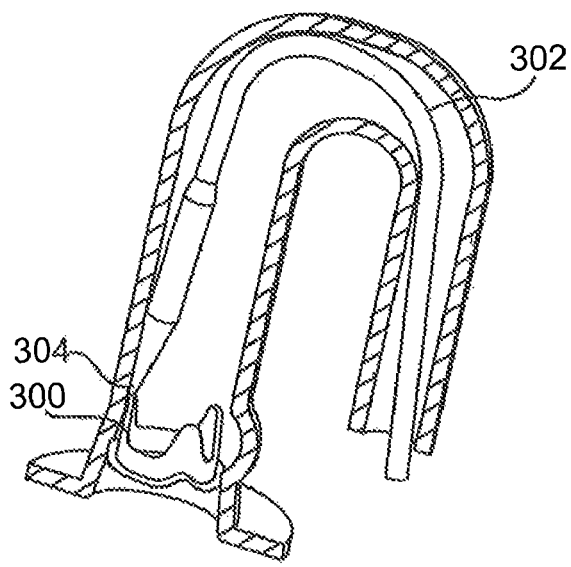
FIGS. 21-23 are partial cross-sectional side views of three sequential steps for delivering a stent to a prosthetic heart valve, including a delivery system centering feature.
Figure 22:
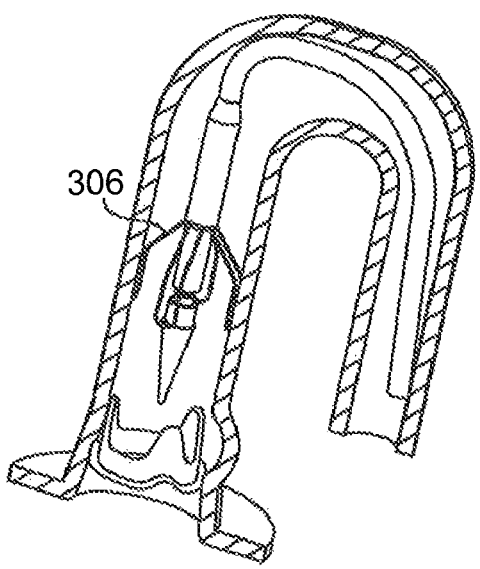
Figure 23:
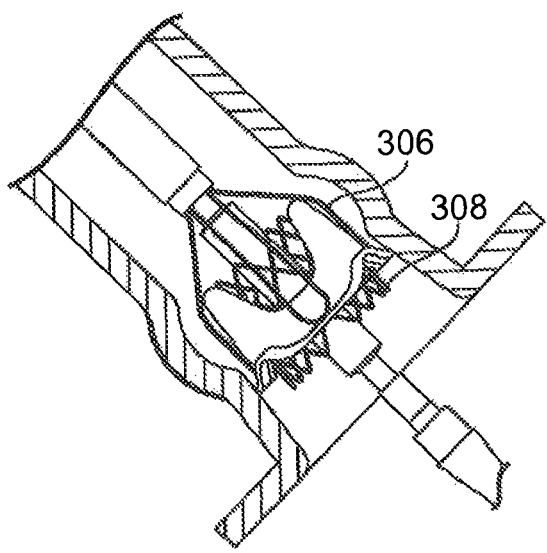

The deployment of petal structures described above relative to FIG. 20 can also provide a centering function for stent delivery systems, as is illustrated in FIGS. 21-23. In particular, a previously implanted heart valve 300 is shown generally in the aorta, with a distal tip 304 of a delivery system 302 positioned adjacent to the outflow side of heart valve 300. Due to the curved path that the delivery system 302 must take to reach the heart valve 300, the distal tip 304 may tend to rest against the side walls of the aorta, rather than being centered therein, as shown in FIG. 21. Deployment of the stent and/or further advancement of the delivery system 302 from this position may be successful; however, in order to reduce the possibility of the distal tip 304 becoming lodged outside the heart valve 300, the petals 306 can be deployed to push the delivery system 302 toward the center of the aorta, as is shown in FIG. 22. The delivery system 302 can then be advanced through the previously implanted heart valve 300 until the desired position of the delivery system is reached for full deployment of a valved stent 308. This approach to centering a delivery system within an opening can be used in combination with other stent configurations of the invention. Again, this delivery system can alternatively be used to deploy stents in a native annulus of a heart valve, if desired, where the deployed petals will be manipulated to contact a structure of the native anatomy rather than the structure of a previously implanted heart valve.

FIGS. 24-26 illustrate another embodiment of a stent delivery system 310 that includes a different type of centering function. Stent delivery system 310 includes a balloon 312 spaced from its distal tip 314, where the balloon 312 is shown in its deflated state in FIG. 24, with the distal tip 314 resting against the side wall of the aorta in which it is positioned due to the curvature of the aorta and the structure of the delivery system. In order to move the distal tip 314 away from the side wall, the balloon 312 can be inflated until the desired movement is achieved, such as is shown in FIGS. 25 and 26. The balloon can be expanded through inflation (using air, fluid, or the like) or it could be a porous structure such as a Nitinol mesh that allows blood to pass through the device during the centering process. For example, balloon 312 may only be inflated slightly to move the tip 314 a small distance from the vessel wall, where additional inflation of the balloon 312 can center the distal tip 314 of the delivery system relative to the opening in the previously implanted heart valve 316. In any case, the delivery system 310 can then be advanced through the heart valve 316 until the desired position of the system is reached for full deployment of a stent, such as a stent that is the self-expanding type. The balloon 312 may be moveable relative to the remainder of the delivery system such that the distal tip may be moved closer and further from the balloon, such as to maintain the balloon in a more fixed location while moving the distal tip for stent deployment.

Stents described herein may further include at least one location of a radiopaque, echogenic, or MRI visible material to facilitate visual confirmation of proper placement of the stent and/or portions of the delivery system (e.g., at least one of the petals of the delivery system) relative to the previously implanted prosthetic heart valve. Alternatively, other known surgical visual aids can be incorporated into the stent. Such visual aids can be included on at least one flange of the replacement heart valve and at least one stent post of the previously implanted heart valve to provide indicators for proper placement of the stent.

As discussed herein, the various delivery systems of the invention can be used with any of the stent structures described herein, and/or with other stent structures, for replacement of a previously implanted prosthetic heart valve. A number of different stents and delivery systems can be used for such implantations, including the stents and delivery systems described above, along with other exemplary stents and delivery systems, such as those described in U.S. Pat. Application Publication No. 2003/0199963-A1; U.S. patent application Ser. No. 12/070,387, entitled "REPLACEMENT PROSTHETIC HEART VALVES AND METHODS OF IMPLANTATION", filed on even date herewith; U.S. patent application Ser. No. 12/070,380, entitled "DELIVERY SYSTEMS AND METHODS OF IMPLANTATION FOR REPLACEMENT PROSTHETIC HEART VALVES"; filed on even date herewith, and U.S. patent application Ser. No. 12/070,347, entitled "REPLACEMENT PROSTHETIC HEART VALVES AND METHODS OF IMPLANTATION", filed on even date herewith, all of which are incorporated by reference in their entireties.

Referring again to FIG. 1, the stent or valve structure 12 includes a sewing ring 14 and stent posts 16 and is covered by a covering 18, such as is included in the stented tissue valves commercially available from Medtronic, Inc. of Minneapolis, Minn. under the trade designations "Hancock II" and "Mosaic". A wide variety of other stented tissue valves, such as those described in U.S. Pat. Nos. 4,680,031, 4,892,541, and 5,032,128, the teachings of which are incorporated herein by reference, can be employed as the stent or valve structure 12. Alternatively, the structure 12 can be stentless, such as, for example, a Freestyle stentless bioprosthesis, commercially available from Medtronic, Inc. under the trade designation "Freestyle". Other acceptable stentless configurations are described in U.S. Pat. Nos. 5,156,621; 5,197,979; 5,336,258; 5,509,930; 6,001,126; 6,254,436; 6,342,070; 6,364,905; and 6,558,417, the teachings of which are incorporated herein by reference. Regardless, the leaflets (not shown) are attached to the structure 12 by sewing, crimping, adhesive, etc., for example, and can assume a variety of forms (e.g., autologous tissue, xenograph tissue, or synthetic material, such as polymers, metals, combinations thereof, and the like).

With any of the embodiments of the invention described herein, the valved stents can be placed inside of a failed valve with leaflets, as described herein, or the leaflets of the failed valve can be removed prior to delivery of the new valved stents, in accordance with known procedures for leaflet removal. Exemplary procedures for leaflet removal are described, for example, in U.S. Patent Publication No. 2004/0034380 (Woolfson et al.), and exemplary devices and methods of filtering in conjunction with leaflet removal are described, for example, in U.S. Pat. Nos. 6,896,690 (Lambrecht et al.) and 6,692,513 (Streeter et al.), all of which are incorporated herein by reference. In this way, the leaflets of the failed bioprosthesis cannot interfere with the leaflets of the newly implanted valved stent and particulates from the leaflet removal can be filtered from the blood of the patient.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method of delivering a replacement prosthetic valve to a previously implanted prosthetic valve comprising an inflow end and an outflow end, the method comprising:
   compressing a replacement prosthetic valve comprising an expandable stent within a first sheath of a delivery system, wherein the delivery system comprises a proximal end and a distal end;
   advancing the distal end of the delivery system and compressed replacement prosthetic valve into a vessel of a patient and toward the outflow end of the previously implanted prosthetic valve until the compressed expandable stent has advanced through the previously implanted prosthetic valve and is positioned past the inflow end of the previously implanted prosthetic valve;

partially retracting a second sheath of the delivery system toward the proximal end of the delivery system until at least one petal of the delivery system extends from a first end of the second sheath, wherein the at least one petal extends radially relative to the sheath;

partially withdrawing the delivery system from the vessel of the patient until the at least one petal engages with the inflow end of the previously implanted prosthetic valve; and retracting the first sheath of the delivery system toward the proximal end of the delivery system to expose the compressed stent and deploy the replacement prosthetic valve.

2. The method of claim 1, wherein the at least one petal of the delivery system comprises a plurality of petals.

3. The method of claim 1, wherein the expandable stent comprises a self-expanding material that is expandable from a compressed state to an expanded state in response to removal of at least one compressive force.

4. The method of claim 1, wherein the step of retracting the second sheath of the delivery system further comprises retracting the sheath until the at least one petal is biased toward the proximal end of the delivery system.

5. The method of claim 1, further comprising the steps of disengaging the delivery system from the deployed replacement prosthetic valve and removing the delivery system from the patient.

6. The method of claim 1, wherein the previously implanted prosthetic valve comprises an aortic valve and wherein the step of advancing the delivery system further comprises advancing the distal end of the delivery system through the aorta to the aortic valve.

7. The method of claim 6, wherein the inflow end of the previously implanted prosthetic valve comprises the inflow side of the aortic valve.

* * * * *